(12) United States Patent
Yodfat et al.

(10) Patent No.: US 9,173,993 B2
(45) Date of Patent: Nov. 3, 2015

(54) FLUID DELIVERY DEVICE

(75) Inventors: Ofer Yodfat, Maccabim-Reut (IL);
Avraham Neta, Misgav (IL); Doron Bushi, Holon (IL); Illai Gescheit, Tel Aviv (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 69 days.

(21) Appl. No.: 12/451,427

(22) PCT Filed: May 11, 2008

(86) PCT No.: PCT/IL2008/000643
§ 371 (c)(1),
(2), (4) Date: Nov. 12, 2009

(87) PCT Pub. No.: WO2008/139460
PCT Pub. Date: Nov. 20, 2008

(65) Prior Publication Data
US 2010/0130931 A1    May 27, 2010

Related U.S. Application Data

(60) Provisional application No. 60/928,750, filed on May 11, 2007, provisional application No. 60/928,751, filed on May 11, 2007, provisional application No. 60/928,815, filed on May 11, 2007.

(51) Int. Cl.
*A61M 5/148* (2006.01)
*A61M 5/145* (2006.01)
(Continued)

(52) U.S. Cl.
CPC ........ *A61M 5/14248* (2013.01); *F04B 43/1269*
(2013.01); *A61M 5/148* (2013.01); *A61M 5/1452* (2013.01); *A61M 2005/14268* (2013.01);
(Continued)

(58) Field of Classification Search
CPC ............... A61M 5/14586; A61M 5/14593;
A61M 5/148; A61M 5/14583; A61M 5/152;
A61M 2005/14268; A61M 2205/3569; A61M 2205/3592; A61M 5/14248; A61M 5/1452;
F04B 43/1269; F04B 43/1276
USPC ........... 604/151–155, 500, 67, 131–132, 142
See application file for complete search history.

(56) References Cited

U.S. PATENT DOCUMENTS 2,168,080 A * 8/1939 Allen ........................... 222/101
3,017,883 A * 1/1962 Dickinson, Jr. ............. 604/404
3,151,616 A * 10/1964 Selfon ......................... 604/131

(Continued)

FOREIGN PATENT DOCUMENTS

DE    39 42 493    12/1989
EP    0 170 784    4/1985

(Continued)

OTHER PUBLICATIONS

International Search Report for PCT/IL2008/000643.

*Primary Examiner* — Quynh-Nhu H Vu
(74) *Attorney, Agent, or Firm* — Dinsmore & Shohl LLP

(57) ABSTRACT

A method and an apparatus for delivery of a therapeutic fluid to the body of a patient are provided. The apparatus includes a dispensing unit having a driving mechanism and a pumping mechanism for pumping the fluid to the body of the patient and a collapsible reservoir fillable with the therapeutic fluid for delivery thereof to the body of the patient.

17 Claims, 23 Drawing Sheets

(51) Int. Cl.
   *A61M 5/142*   (2006.01)
   *F04B 43/12*   (2006.01)

(52) U.S. Cl.
   CPC .............. *A61M2205/3569* (2013.01); *A61M 2205/3592* (2013.01)

(56) References Cited

U.S. PATENT DOCUMENTS

| | | | | |
|---|---|---|---|---|
| 3,631,847 | A | 1/1972 | Hobbs | 128/2 R |
| 3,771,694 | A | 11/1973 | Kaminski | 222/70 |
| 3,884,228 | A * | 5/1975 | Hahn | 604/131 |
| 4,019,665 | A * | 4/1977 | Ritter et al. | 226/112 |
| 4,234,104 | A * | 11/1980 | Apuzzo et al. | 222/94 |
| 4,280,637 | A | 7/1981 | Runciman | 222/39 |
| 4,396,385 | A * | 8/1983 | Kelly et al. | 604/152 |
| 4,498,843 | A * | 2/1985 | Schneider et al. | 417/22 |
| 4,525,164 | A * | 6/1985 | Loeb et al. | 604/131 |
| 4,544,369 | A | 10/1985 | Skakoon et al. | 604/155 |
| 4,657,486 | A | 4/1987 | Stempfle et al. | 417/12 |
| 4,715,786 | A | 12/1987 | Wolff et al. | 417/22 |
| 5,000,739 | A * | 3/1991 | Kulisz et al. | 604/132 |
| 5,048,725 | A * | 9/1991 | Peterson | 222/100 |
| 5,692,645 | A * | 12/1997 | Ryu | 222/101 |
| 5,775,540 | A * | 7/1998 | Greenberg | 222/102 |
| 5,957,895 | A | 9/1999 | Sage et al. | 604/181 |
| 6,394,981 | B2 * | 5/2002 | Heruth | 604/140 |
| 6,485,461 | B1 | 11/2002 | Mason et al. | 604/132 |
| 6,485,471 | B1 | 11/2002 | Zivitz et al. | 604/212 |
| 6,589,229 | B1 | 7/2003 | Connelly et al. | 604/890.1 |
| 6,723,072 | B2 | 4/2004 | Flaherty et al. | 604/131 |
| 6,726,655 | B1 * | 4/2004 | Lieberman et al. | 604/131 |
| 6,740,059 | B2 | 5/2004 | Flaherty | 604/67 |
| 7,686,787 | B2 * | 3/2010 | Moberg et al. | 604/155 |
| 7,794,434 | B2 * | 9/2010 | Mounce et al. | 604/216 |
| 2001/0016710 | A1 * | 8/2001 | Nason et al. | 604/153 |
| 2002/0169439 | A1 | 11/2002 | Flaherty | 604/891.1 |
| 2003/0158508 | A1 * | 8/2003 | DiGianfilippo et al. | 604/4.01 |
| 2003/0198558 | A1 | 10/2003 | Nason et al. | 417/53 |
| 2007/0106218 | A1 | 5/2007 | Yodfat et al. | 604/131 |
| 2008/0215035 | A1 | 9/2008 | Yodfat et al. | 604/513 |

FOREIGN PATENT DOCUMENTS

| | | |
|---|---|---|
| GB | 2304584 | 3/1997 |
| WO | WO 2006/108809 | 10/2006 |
| WO | WO 2006/121921 | 11/2006 |
| WO | WO 2008/139458 | 11/2008 |
| WO | WO 2008/139459 | 11/2008 |

* cited by examiner

FLUID DELIVERY DEVICE

CROSS-REFERENCE TO RELATED APPLICATIONS

The present application is a 35 U.S.C. §371 national stage entry of PCT/IL2008/000643, which has an international filing date of May 11, 2008 and claims priority to U.S. Provisional Patent Application Nos. 60/928,750, 60/928,751 and 60/928,815, all of which were filed in the U.S. Patent & Trademark Office on May 11, 2007. The present application incorporates herein by reference the disclosure of each of the above-referenced applications in its entirety.

The present application relates to co-pending/co-owned U.S. patent application Ser. No. 12/451,430, and International Patent Application No. PCT/IL2008/000642, both entitled "Methods And Apparatus For Monitoring Rotation Of An Infusion Pump Driving Mechanism" and claiming priority to U.S. Provisional Patent Application No. 60/928,751, filed on May 11, 2007, entitled "Methods And Apparatus For Monitoring Rotation Of An Infusion Pump Driving Mechanism". The present application also relates to U.S. patent application Ser. No. 12/451,435, and International Patent Application No. PCT/IL2008/000641, both entitled "A Positive Displacement Pump", and claiming priority to U.S. Provisional Patent Application No. 60/928,815, filed on May 11, 2007 entitled "A Positive Displacement Pump". This application incorporates disclosures of each of these applications herein by reference in their entireties.

FIELD OF THE INVENTION

The present invention relates generally to methods, systems and devices for sustained medical infusion of fluids, and in particular, to a device configured as a miniature portable infusion patch that can be attached to the body of a patient, and to methods and devices for the accurate dispensing of fluids into the body of the patient. More particularly, the present invention relates to a patch-like dispensing unit that includes two separate parts, such as a disposable part and a reusable part, where the disposable part includes a flexible reservoir and the reusable part includes a metering apparatus for accurately dispensing fluids from the reservoir.

BACKGROUND OF THE INVENTION

Medical treatment of several illnesses requires continuous drug infusion into various body compartments, such as subcutaneous and intra-venous injections. Diabetes mellitus patients, for example, require administration of varying amounts of insulin throughout the day to control their blood glucose levels. In recent years, ambulatory portable insulin infusion pumps have emerged as a superior alternative to multiple daily syringe injections of insulin. These pumps, which deliver insulin at a continuous basal rate as well as in bolus volumes, were developed to liberate patients from repeated self-administered injections, and allow them to maintain a near-normal daily routine. Both basal and bolus volumes must be delivered in precise doses, according to individual prescription, since an overdose or under-dose of insulin could be fatal. Therefore, insulin injection pumps must feature high reliability, totally preventing delivery of any unintentional insulin excess.

Several ambulatory insulin infusion devices are currently available on the market. Mostly, these devices have two portions: a reusable portion that contains a dispenser, a controller and electronics, and a disposable portion that contains a syringe-type reservoir, a needle assembly with a cannula and a penetrating member, and fluid delivery tube. Usually, the patient fills the reservoir with insulin, attaches the needle and the delivery tube to the exit port of the reservoir, and then inserts the reservoir into the pump housing. After purging air out of the reservoir, tube and needle, the patient inserts the needle assembly, penetrating member and cannula, at a selected location on the body, and withdraws the penetrating member. To avoid irritation and infection, the subcutaneous cannula should be replaced and discarded after 2-3 days, together with the empty reservoir. Examples of first generation disposable syringe-type reservoir and tubes were disclosed in U.S. Pat. No. 3,631,847 to Hobbs, U.S. Pat. No. 3,771,694 to Kaminski, U.S. Pat. No. 4,657,486 to Stempfle, and U.S. Pat. No. 4,544,369 to Skakoon. The driving mechanism of these devices is a screw thread driven plunger controlling the programmed movement of a syringe piston.

Other dispensing mechanisms have been also discussed, including peristaltic positive displacement pumps, in U.S. Pat. No. 4,498,843 to Schneider and U.S. Pat. No. 4,715,786 to Wolff. These devices represent an improvement over multiple daily injections, but nevertheless, they all suffer from several drawbacks. The main drawback is the large size and the weight of the device, caused by the configuration and the relatively large size of the driving mechanism of the syringe and the piston. This relatively bulky device has to be carried in a patient's pocket or attached to the belt. Consequently, the fluid delivery tube is long, usually longer than 60 cm, in order to permit needle insertion at remote sites of the body. These uncomfortable bulky devices with a long tube are rejected by the majority of diabetic insulin users, since they disturb regular activities, such as sleeping and swimming. Further, the effect of the image projected on the teenagers' body is unacceptable. In addition, the delivery tube excludes some optional remote insertion sites, like buttocks, arms and legs.

To avoid the consequences of long delivery tube, a new concept, of second generation pump, was proposed. This concept includes a remote controlled skin adherable device with a housing having a bottom surface adapted to contact patient's skin, a reservoir disposed within the housing, and an injection needle adapted to communicate with the reservoir. These skin adherable devices should be disposed every 2-3 days similarly to available pump infusion sets. These devices were disclosed at least in U.S. Pat. No. 5,957,895 to Sage, U.S. Pat. No. 6,589,229 to Connelly, and U.S. Pat. No. 6,740,059 to Flaherty. Additional configurations of skin adherable pumps were disclosed in U.S. Pat. No. 6,723,072 to Flaherty and U.S. Pat. No. 6,485,461 to Mason. These devices also have several limitations: they are bulky and expensive, their high selling price is due to the high production and accessory costs, and the user must discard the entire device every 2-3 days, including relatively expensive components, such as driving mechanism and other electronics.

Further, a syringe-type reservoir has at least the following limitations:
- It has a round cross section, which increases the device thickness because of inefficient use of space.
- Relatively high rotational momentum is required for displacement of the syringe due to the high friction associated with the round gasket and the high surface-area ratio of the plunger and outlet port.
- It is difficult to achieve highly accurate dispensing rates because minimal plunger movements cause large amounts of dispensed fluid.

Thus, there is a need for a fluid dispensing device that would avoid the above limitations and disadvantages of conventional units.

SUMMARY OF THE INVENTION

Some embodiments of the present invention relate to a dispensing unit that includes two parts, a disposable and a reusable, and subsequent to their connection the entire unit has a thin profile. The disposable part has a reservoir allowing manual filling and purging of air. The reusable part of the dispensing unit that has a metering portion. Upon connection of the two parts the metering portion allows fluids to be dispensed from the reservoir according to a programmed or "on demand" instructions. The reservoir has thin walls and allows the metering portion to precisely dispense fluid by applying minimal force and maintaining high dispensing accuracy.

Some of the embodiments present invention relate to a device and a method for continuous delivery of therapeutic fluid (e.g., insulin), into the body of the patient via a cannula. The device includes a dispensing unit that can be disconnected from and reconnected to a needle unit. Insulin delivery programming can be done using a remote control unit or directly by manual buttons provided on the dispensing unit. Fluid pumping is achieved by pushing upon a flexible reservoir filled with the therapeutic fluid.

In some embodiments, the present invention relates to a method, a system and a device for the sustained medical infusion of therapeutic fluids into the body, in a programmed mode ensuring highly accurate doses delivered by an infusion device.

In some embodiments, the present invention relates to a method for sustained medical infusion at a controlled rate, having the following steps:
  providing a reusable part of the dispensing unit, having:
    a control unit and a transceiver for managing operations and for communication;
    a driving mechanism for generating movement of a dispensing mechanism/element, wherein the driving mechanism is controllable using a control unit and the transceiver;
    a main portion of the dispensing mechanism/element operated by the driving mechanism, the dispensing element becoming operative for transfer of fluid when the main portion is coupled with a secondary portion (in some embodiments, the dispensing element is a plunger);
  providing a disposable part of the dispensing unit, having:
    the secondary portion of the dispensing element, for coupling with the main portion;
    a reservoir, which can be filled with a fluid to be infused into the body of the patient;
    an outlet port (i.e., a well assembly, an infusion set, a cannula, a needle, etc.);
    a tube for fluid communication of the reservoir and the outlet port (in some embodiments);
  providing a remote control unit for programming, data acquisition and data downloading.

In some embodiments, the present invention relates to a method for sustained medical infusion, wherein the main portion of the dispensing unit is contained in a first part, the secondary portion of the dispensing unit is disposed in a second part, and coupling of the first part in operative association with the second part enables the dispensing unit to dispense fluid from the reservoir.

In some embodiments, the present invention relates to a method for sustained medical infusion wherein the first part and the second part of the dispensing unit are each configured as skin compliant housings, and at least one part can be attached to and/or detached from the skin. In some embodiments, the dispensing unit is connected to a skin adherable needle unit and it can be connected and disconnected upon patient's discretion.

In some embodiments, the present invention relates to a method for sustained medical infusion where one part of the dispensing unit contains a fluid metering apparatus. The apparatus includes a plunger or a roller that can be displaced outwardly from the reusable part. The plunger/roller can be displaced by a gear box driven by a DC motor, or a stepper motor or a Shape Memory Alloy (SMA) actuator.

In some embodiments, the present invention includes a sac-like reservoir contained in the disposable part. The reservoir is flexible, expands during filling, and shrinks during dispensing. It has an inlet port and an exit port. The inlet port is sealed by a self-sealing rubber-like material that allows filling with a sharp needle and remains sealed after needle withdrawal. The exit port of the reservoir is connected to the outlet port of the disposable part, which is then connected to dedicated means that allow infusion of fluid into the body of the patient. Examples of such means could be a ""well"" assembly, a Luer lock adapter, a delivery tube, etc.

After connection of the reusable and disposable parts, the reservoir comes in contact with the plunger/roller contained in the reusable part. In some embodiments, the resilient reservoir is pushed upon by the plunger, which gradually urges the fluid to be dispensed through the outlet port. The reservoir has thin walls, which can be folded inwardly ("reverse sock effect"), thus constantly maintaining reservoir sealing and avoiding high friction forces.

In some embodiments, the invention relates to a "stand alone" reservoir that is not attached to the disposable part. In some embodiments, the "stand alone" reservoir can be connected to the well assembly directly or via a short tube. After connection of the disposable and reusable parts, the reservoir is plugged in between the parts: on one side, it contacts with the plunger, and on the other side, it is connected to the well, for example.

In some embodiments, the reservoir has no inside sliding rigid elements (as opposed to conventional syringe-type reservoirs), thus, avoiding friction and reducing the required driving forces and moments.

In some embodiments, the present invention relates to a method for sustained medical infusion, wherein the main portion of the dispensing element exerts pressure on the reservoir only when coupled with the secondary dispensing element. The pressure exerted on the reservoir causes fluid to be dispensed. In some embodiments, the reservoir can be filled manually and air can be manually purged out of the reservoir.

In some embodiments, the present invention relates to devices for sustained medical infusion with a controlled rate of injection of a fluid into the body of the patient, the devices having:
  a first separate reusable part of a dispensing unit, including:
    a control unit and a transceiver for managing operations and for communication;
    a driving mechanism for generating movement of a dispensing mechanism/element, where the driving mechanism is controllable by the control unit and the transceiver;
    a main portion of the dispensing mechanism/element operated by the driving mechanism, the dispensing element becoming operative for transferring fluid, when the main portion is coupled to a secondary portion of the dispensing mechanism/element;
  a second separate disposable part of the dispensing unit, including:

the secondary portion of the dispensing element, for coupling with the main portion;

a reservoir, which can be filled with a fluid to be infused into the body of the patient;

an outlet port (i.e., a well assembly, an infusion set, a cannula, a needle, etc.);

a tube for fluid communication of the reservoir and the outlet port (in some embodiments); and a remote control unit for programming, data acquisition and data downloading.

DETAILED DESCRIPTION OF THE INVENTION

Figure 1A:
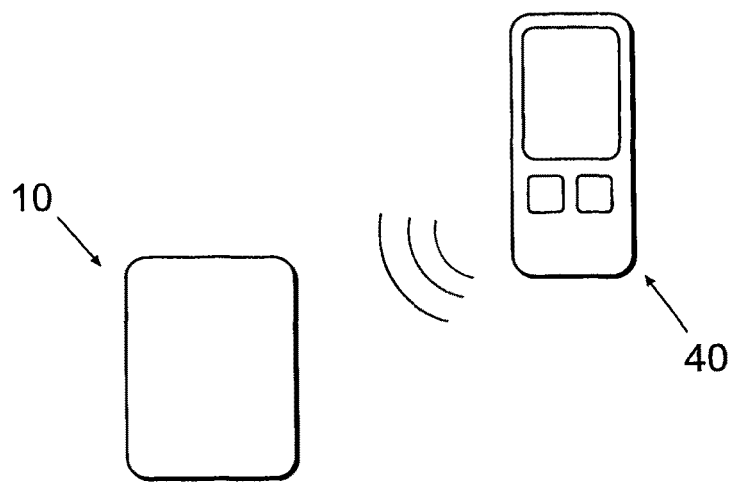
FIGS. 1a-c illustrate exemplary single-part dispensing unit and a two-part dispensing unit along with a remote control unit, according to some embodiments of the present invention.
Figure 1B:
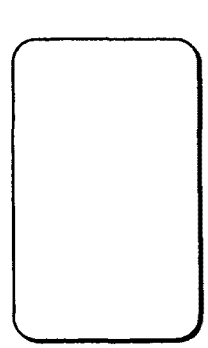
Figure 1C:
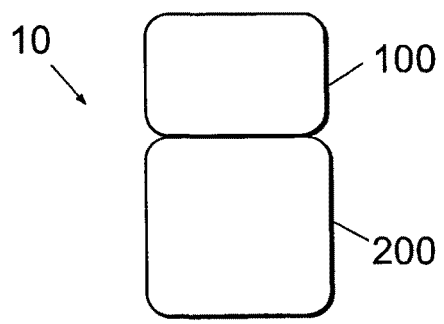

FIG. 1a shows a fluid delivery device having a dispensing unit (10) and a remote control unit (40), according to some embodiments of the present invention. The dispensing unit (10) communicates with the remote control unit (40) that can forward commands, receive and process instructions from the dispensing unit (10), etc. The remote control unit (40) can include a display and a plurality of buttons to control operation of the units (10) and (40). The units (10) and (40) can communicate with a wireless, wired, wire line, RF or any other type communication. The unit (40) can be a personal computer, a laptop, an iPod, a PDA, a cellular telephone, a remote control, or any other suitable device. In some embodiments, the dispensing unit (10) has a single part (as shown in FIG. 1b) or two parts (as shown in FIG. 1c), i.e., a reusable part (100) and a disposable part (200), which can be connected with the reusable part (100).

Figure 2A:
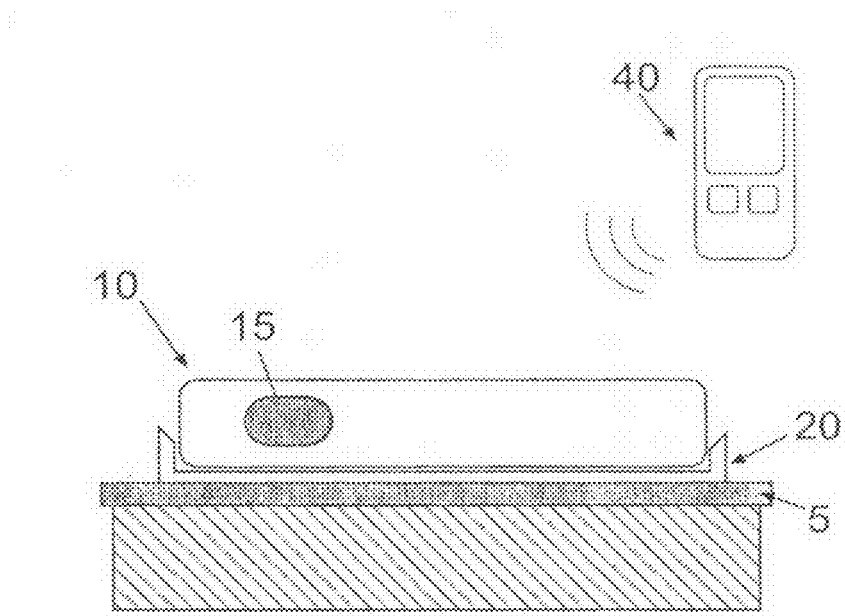
FIGS. 2a-b illustrate exemplary single-part dispensing unit, a two-part dispensing unit, a remote control unit and a needle unit, according to some embodiments of the present invention.

FIG. 2a shows the fluid delivery device having a single-part dispensing unit (10), a needle unit (20) and a remote control unit (40). The needle unit (20) can be adhered to skin (5) of the patient through the use of adhesives. The dispensing unit (10) is connected to the needle unit (20) after adherence of the needle unit (20) to the patient's skin (5).

In some embodiments, fluid delivery can be programmed solely by a remote control unit (40) having a bidirectional communication link with the transceiver provided in the dispensing unit (10). In some embodiments, infusion programming can be carried out by a remote control unit (40) and/or by manual buttons (15) provided on the dispensing unit (10).

Figure 2B:
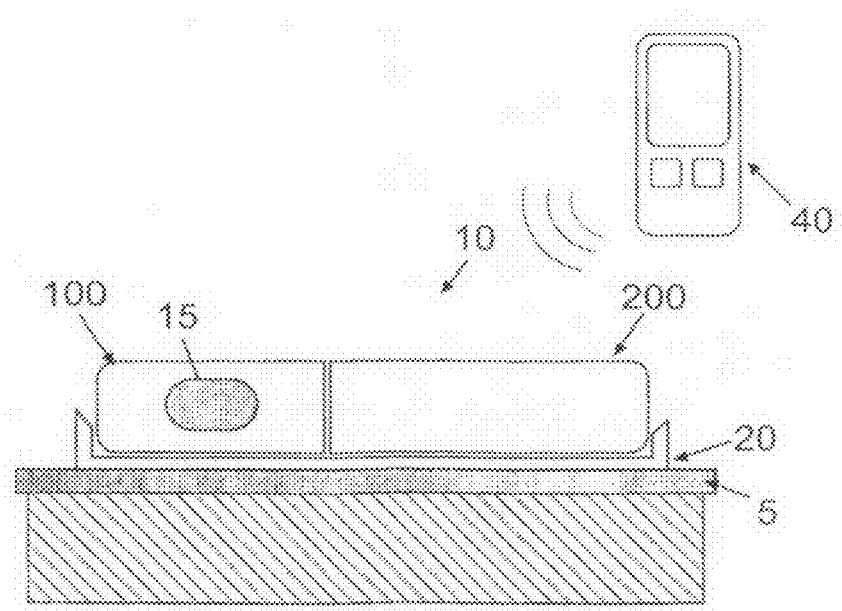

FIG. 2b shows the fluid delivery device having a two-part dispensing unit (10), a needle unit (20) and a remote control unit (40). As above, the needle unit (20) is adhered to the skin (5) of the patient, and the dispensing unit (10) is secured to the needle unit (10). The remote control unit (40) communicates with the dispensing unit (10) to implement infusion programming, data collection, and/or data acquisition. As shown in FIG. 2b, the manual buttons (15) are located on the reusable part (100) of the dispensing unit (10).

Figure 3A:
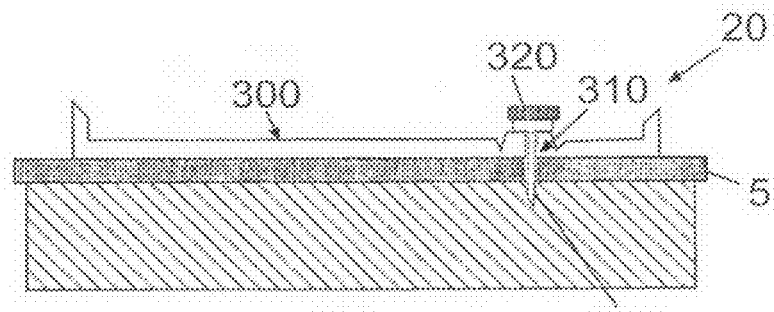
FIGS. 3a-b illustrate an exemplary needle unit having a cradle, a well and a cannula, according to some embodiments of the present invention.
Figure 3B:
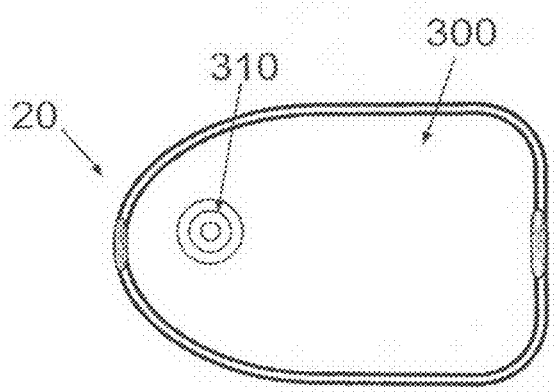

FIGS. 3a-b are side and upper views, respectively, of the needle unit (20). The needle unit includes a cannula (330), a penetrating member (320), a cradle (300), and a well (310). The cannula (330) can be rigidly attached to the cradle (300) and inserted under the skin (5) together with the penetrating member (320). Insertion of the penetrating member (320) and the cannula (330) can be done concurrently with adherence of the cradle (300) to the skin (5). Alternatively, the insertion of the penetrating member (320) and the cannula (330) can be performed subsequently to the cradle (300) being adhered to the skin (5) of the patient. Once the cannula (330) is inserted under the skin of the patient, the penetrating member (320) can be removed from the skin (5) and thereby from needle unit (20). In some embodiments, the cradle (300) is a sheet having an adhesive layer facing the skin (5). The cradle (300) includes an anchoring means on the cradle's upper side for connecting and disconnecting the dispensing unit and the cradle (300). The cradle (300) anchors the cannula (330) and affixes the dispensing unit (not shown). In some embodiments, the cradle (300) can be rigidly connected to the cannula (330) and the well (310). In other embodiments, the cradle (300) can be a separate, stand-alone item. In some embodiments, the well (310) is a tubular protrusion extending upwardly from the cradle (300) to allow alignment with the dispensing unit (not shown) and appropriate connection between the needle unit (20) and the dispensing unit for proper fluid delivery to the body of the patient. Various embodiments for attaching the needle unit (20) and its components to the body of the patient were disclosed in co-owned/co-pending U.S. patent application Ser. No. 12/004, 837, and International Patent Application No. PCT/IL07/001578, both filed on Dec. 20, 2007, and claiming priority to U.S. Provisional Patent Application No. 60/876,679, filed on Dec. 22, 2006, the disclosures of which are incorporated herein by reference in their entireties.

Figure 4:
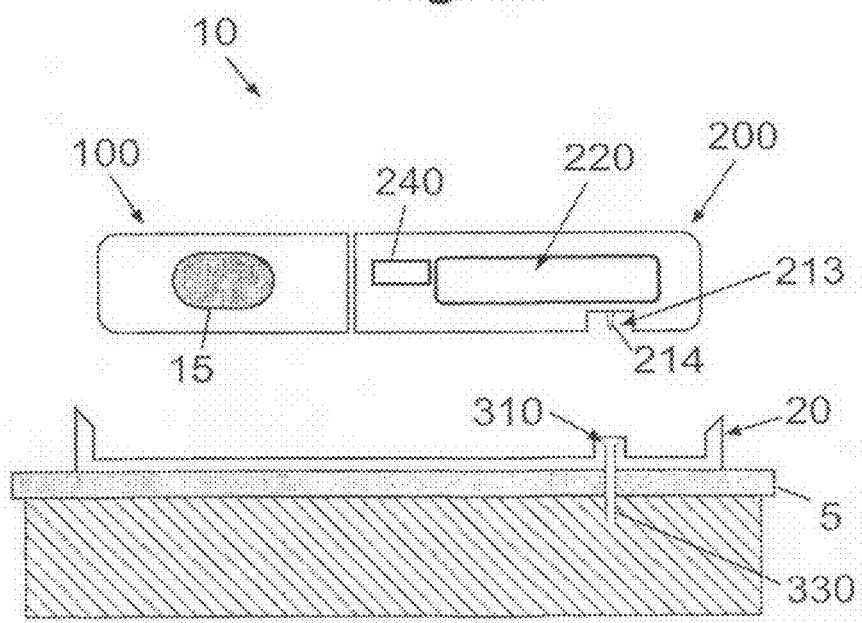
FIG. 4 illustrates the dispensing unit and the needle unit before connection, according to some embodiments of the present invention.

FIG. 4 shows a two-part dispensing unit (10) having an energy supply (240), a fluid reservoir (220), an outlet port (213) and a connecting lumen (214) that maintains fluid communication between the reservoir (220) and the outlet port (213). In some embodiments, all of these components are disposed in the disposable part (200) of the dispensing unit (10). The fluid reservoir (220) contains therapeutic fluid (e.g., insulin) for dispensing to the body of the patient. The reservoir (220) is in fluid communication with the outlet port (213) through which fluid is delivered to the patient. The unit (10) also includes a driving mechanism (not shown in FIG. 4) for causing the fluid to be delivered to the patient. The driving mechanism receives operating instructions from an electronics component (not shown in FIG. 4). The power supply (240) provides power to the driving mechanism and the electronics component. In some embodiments, the electronics component can include a processor, a memory, a transceiver, and any other components. The connecting lumen (214) is disposed at the outlet port (213). Upon connection of the dispensing unit (10) and the needle unit (20), the connecting lumen (214) pierces a septum sealing of the well (310) disposed in the needle unit (20), thus allowing fluid passage and delivery via the cannula (330) to the subcutaneous compartment. The cannula (330) can be previously disposed into the body of the patient with the well (310). The outlet port (213) allows repetitive connection and disconnection of the dispensing unit (10) to and from the needle unit (20).

Figure 5A:
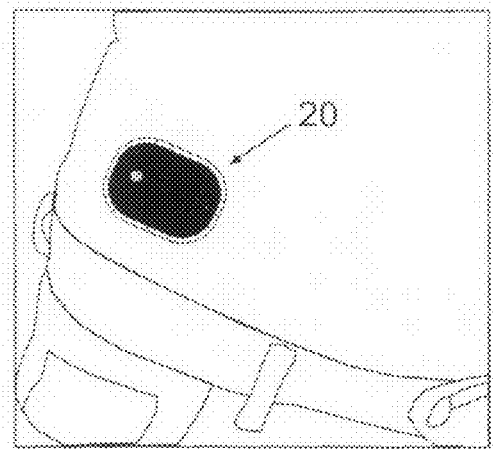
FIGS. 5a-c illustrate an exemplary connection of the dispensing unit to the needle unit, according to some embodiments of the present invention.
Figure 5B:
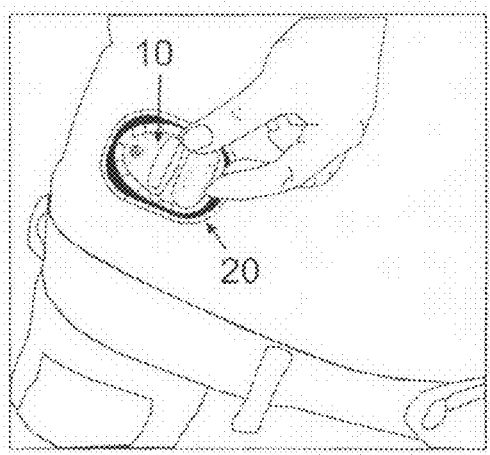
Figure 5C:
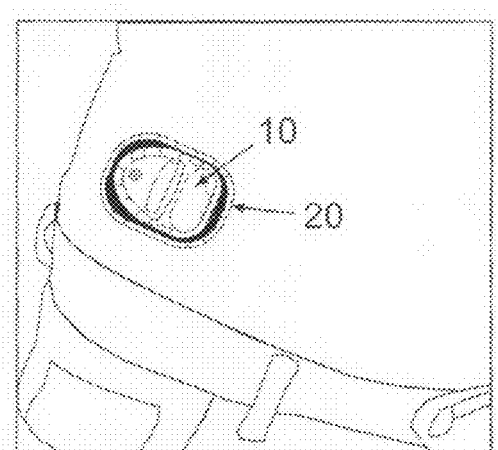

FIGS. 5a-c illustrate the needle unit (20) adhered first to the skin of the patient and the dispensing unit (10) can be then connected to and disconnected from the needle unit (20) upon patient's discretion. FIG. 5a shows the needle unit (20) adhered to the patient's skin. FIG. 5b shows the connection of the dispensing unit (10) to the adhered needle unit (20). FIG. 5c shows the dispensing unit (10) connected to the needle unit (20) and ready for operation.

Figure 6A:
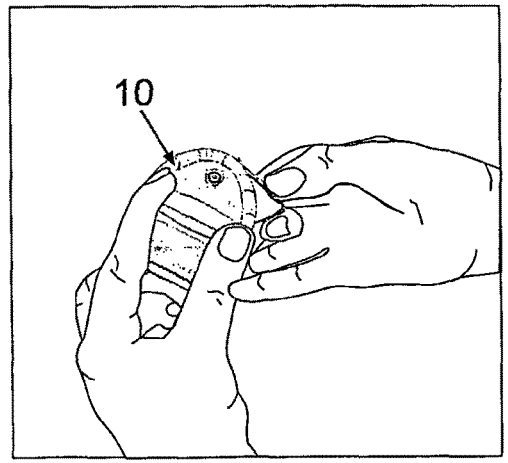
FIGS. 6a-c illustrate the dispensing unit being directly adhered to the skin of the patient, according to some embodiments of the present invention.
Figure 6B:
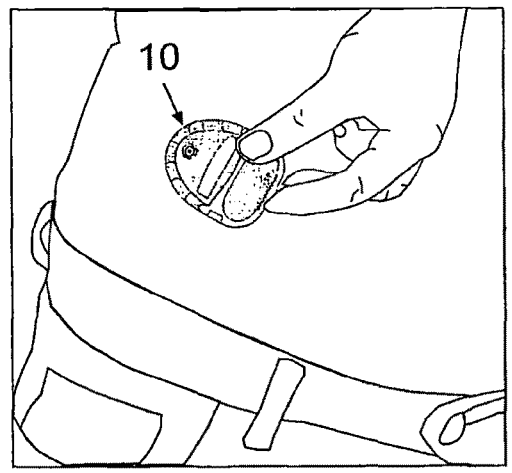
Figure 6C:
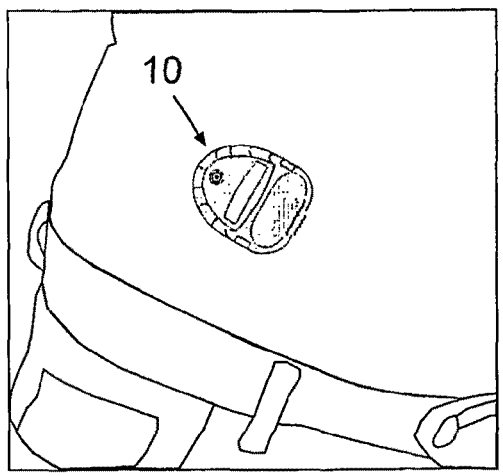

In some embodiments, as shown in FIGS. 6a-c, the dispensing unit (10) is directly adhered to the patient's skin (5). FIG. 6a shows the peeling of an adhesive protective sheet from the lower face of the dispensing unit (10). FIG. 6b shows adherence of the dispensing unit (10) to the patient's skin (5). FIG. 6c shows the adhered dispensing unit (10) being ready for operation.

Figure 7:
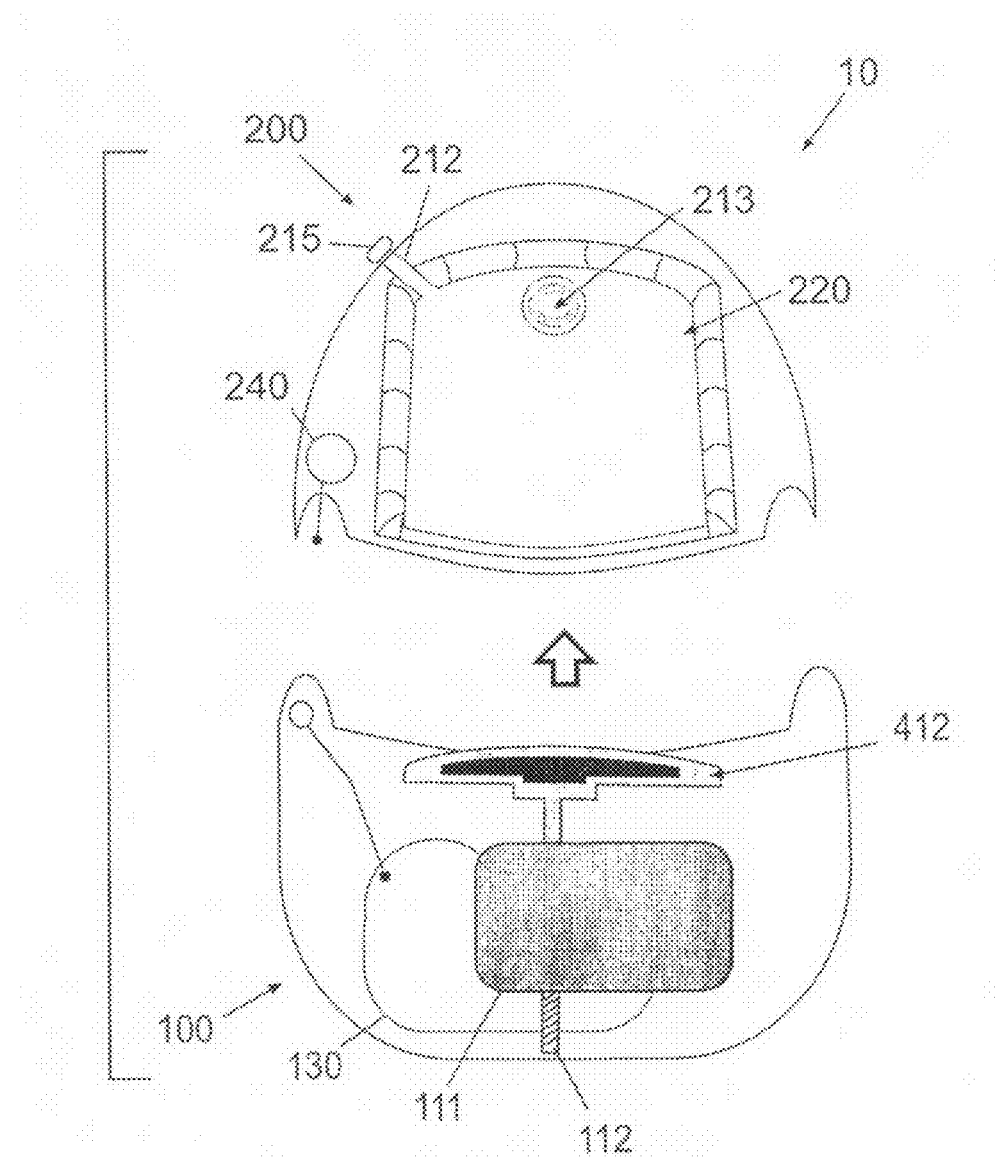
FIG. 7 illustrates exemplary components of the reusable and disposable parts of the dispensing unit, according to some embodiments of the present invention.
Figure 8:
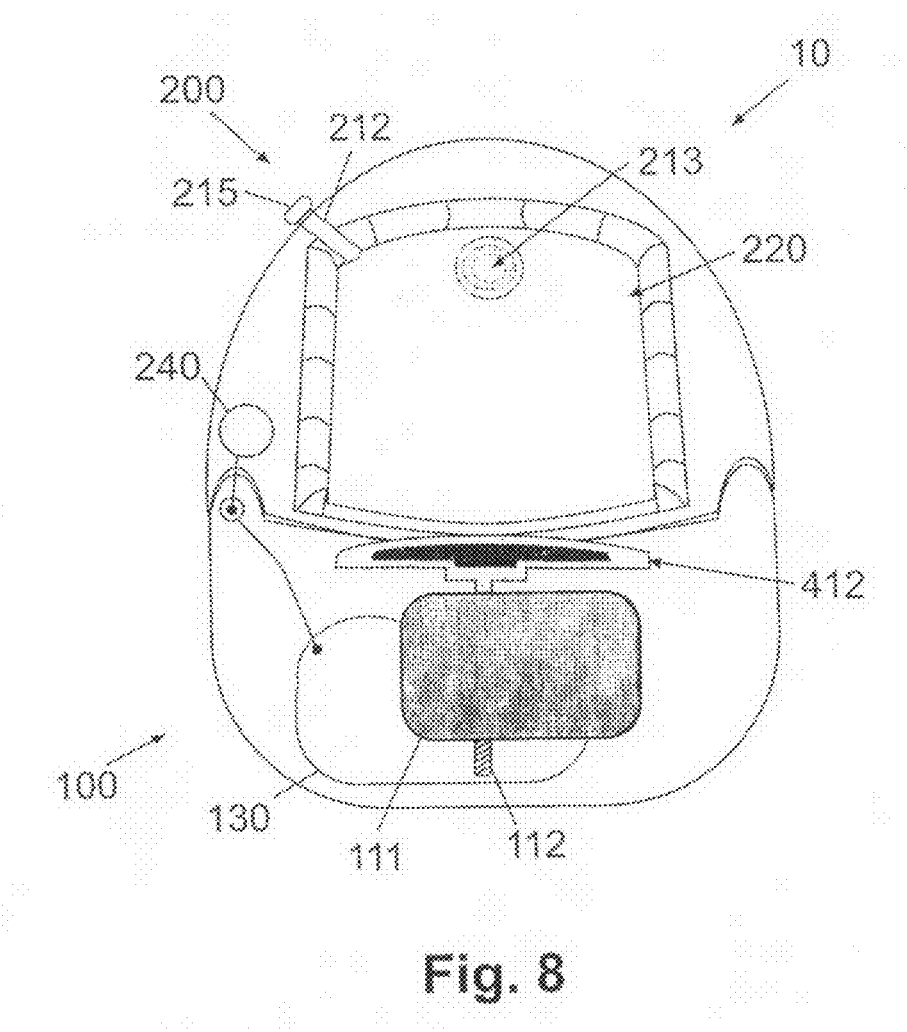
FIG. 8 illustrates an exemplary connection of the reusable and disposable parts of the dispensing unit, according to some embodiments of the present invention.

FIGS. 7-8 illustrate exemplary dispensing unit (10) having the reusable (100) and the disposable parts (200), each contained in a separate dedicated housing, according to some embodiments of the present invention. The reusable part (100) includes a printed circuit board ("PCB") (130) with along various electronic components, a driving mechanism (111), a lead-screw (112) connected to a plunger (412). A rotation monitoring device can also be disposed to monitor rotation/movement of components of the driving mechanism (111), lead-screw (112), and/or plunger (412). In some embodiments, the rotation monitoring device can be a LED coupled with a light detector for detecting light emitted by the LED, or a photointerruptor, or a "Hall effect sensor", etc. Exemplary embodiments of the rotation monitoring device are disclosed in the co-owned/co-pending U.S. patent application Ser. No. 12/451,430, and International Patent Application No. PCT/IL2008/000642, both entitled "Methods And Apparatus For Monitoring Rotation Of An Infusion Pump Driving Mechanism" and claiming priority to U.S. Provisional Patent Application No. 60/928,751, filed May 11, 2007, the disclosures of these applications are incorporated herein by reference. in their entireties.

The disposable part (200) includes the flexible reservoir (220), an inlet port (212), the outlet port (213), and the energy supply (240), e.g., one or more batteries. The reservoir (220) is filled with a therapeutic fluid (e.g., insulin) through the inlet port (212). The reservoir (220) is an enclosed "sac" that is sealed all around, except that it includes the sealable outlet port (213) for dispensing fluid and sealable inlet port (212) for fluid intake. The reservoir (220) can be manufactured from a biocompatible material, e.g., polypropylene, or any other material that does not alter physical and chemical characteristics of the fluid. The inlet port (212) can be sealed by a self-sealing rubber septum (215). The septum (215) allows closure of the inlet port (212) after removal of a filling container/adaptor/connector. The septum further prevents leakage of fluid and entry of contaminants. The disposable part (200) and the reusable part (100) also include a plurality of electrical connectors (e.g., from the PCB (130), power supply (240) etc.) for enabling operation of the dispensing unit (10). Upon connection of the reusable part (100) and the disposable part (200), fluid can be dispensed from the reservoir (220) through the outlet port (213).

The plunger (412) is driven by the driving mechanism (111) and pushes upon the flexible reservoir (220), thereby pushing the fluid from reservoir's open end toward the outlet port (213). The plunger (412) can be disposed within the reusable part (100) or alternatively it can be disposed within the disposable part (200), e.g., adjacent to the reservoir (220). Exemplary driving and pumping mechanisms are disclosed in the in the co-owned/co-pending U.S. patent application Ser. No. 12/451,435, and International Patent Application No. PCT/IL2008/000641, both entitled "A Positive Displacement Pump" and claiming priority to U.S. Provisional Patent Application No. 60/928,815, filed May 11, 2007, entitled "A Positive Displacement Pump", the disclosures of these applications are incorporated herein by reference in their entireties.

Figure 9A:
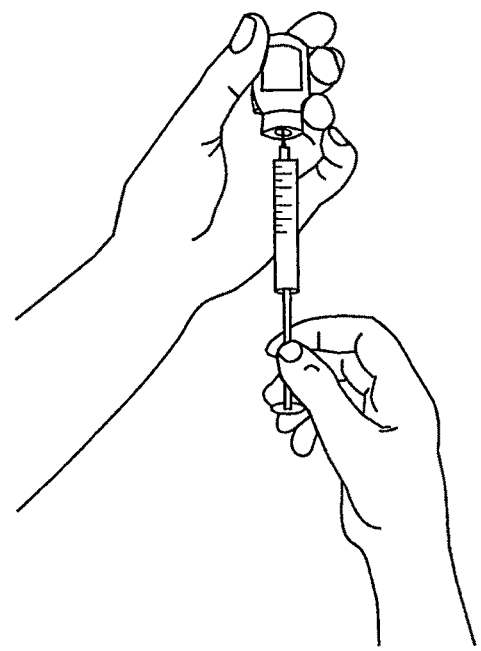
FIGS. 9a-f illustrate exemplary filling and priming stages of a flexible reservoir contained within the disposable part, according to some embodiments of the present invention.
Figure 9B:
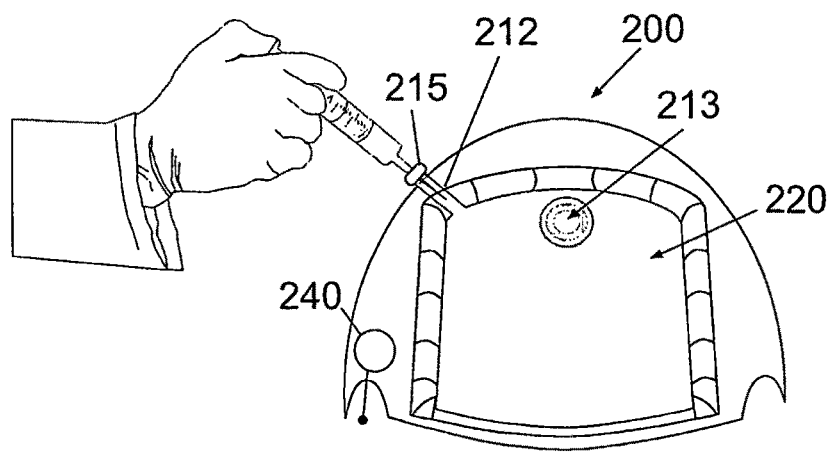
Figure 9C:
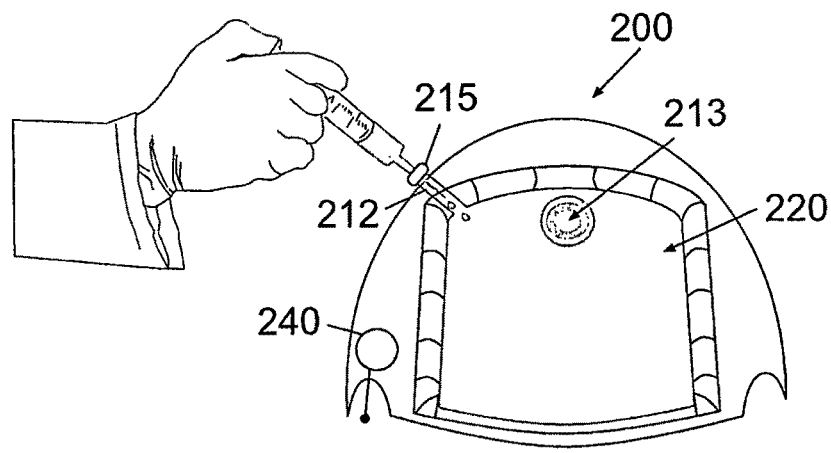
Figure 9D:
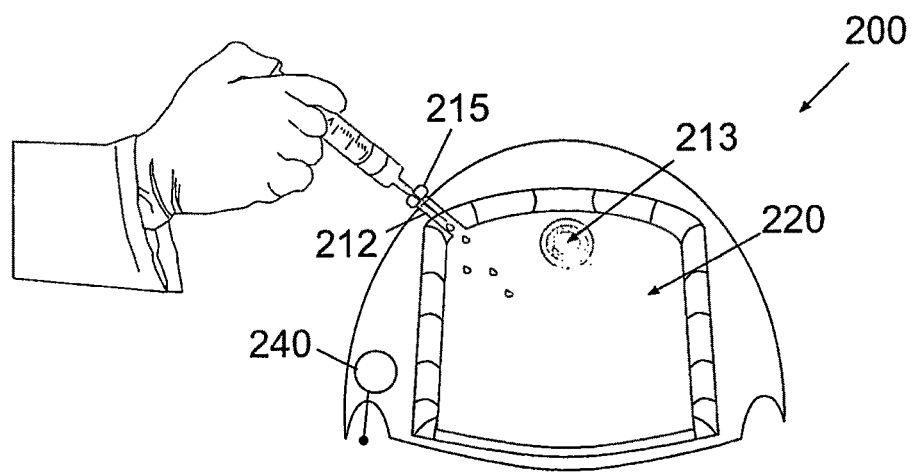
Figure 9E:
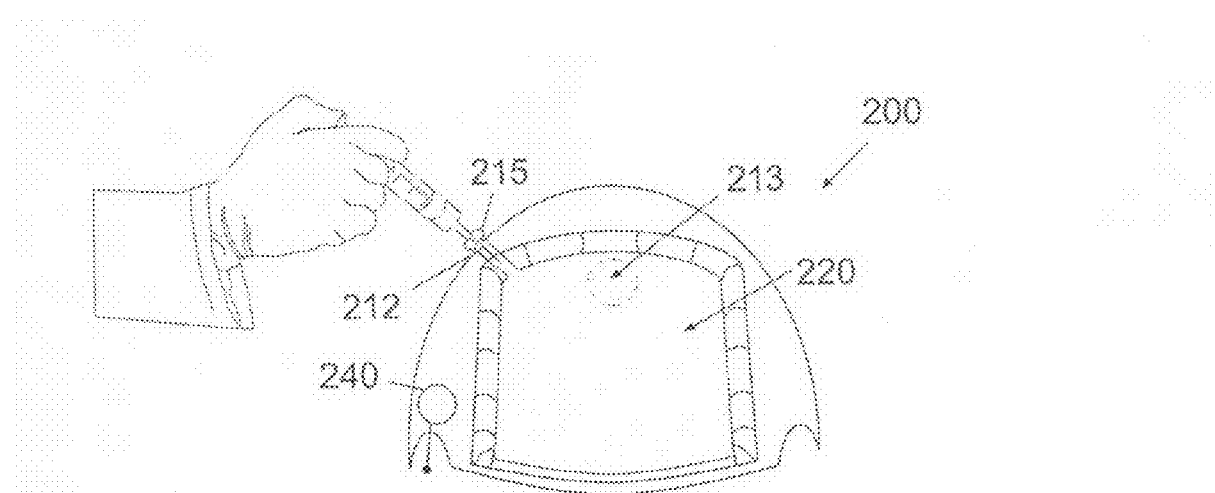
Figure 9F:
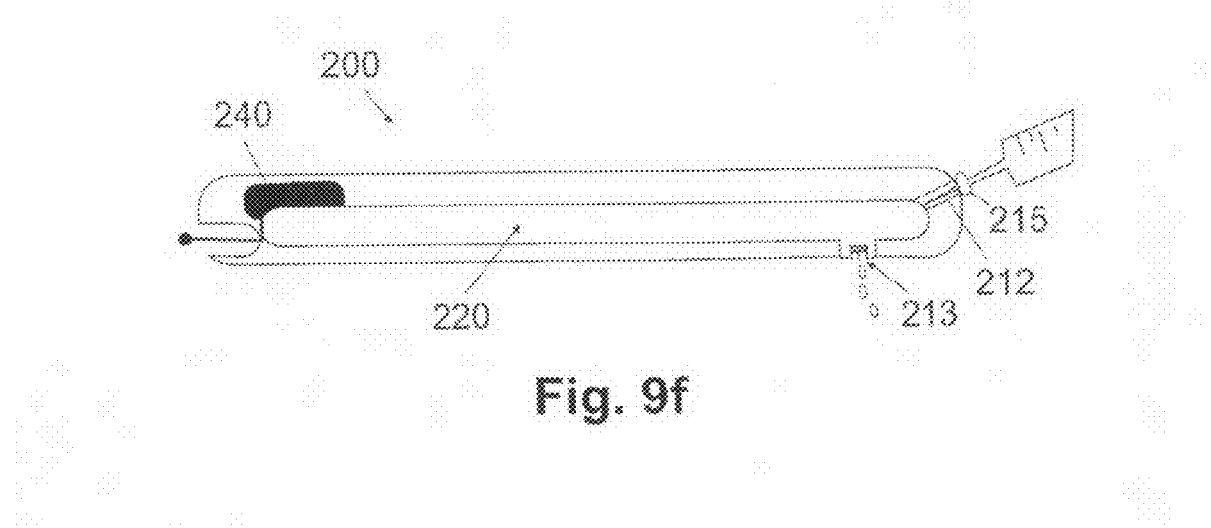

FIGS. 9a-f shows consecutive stages associated with filling the reservoir (220) with therapeutic fluid using a syringe and with priming the reservoir. FIG. 9a illustrates drawing fluid from a bottle containing therapeutic fluid (e.g., insulin) into a syringe. The syringe can be any conventionally known syringe. Once the syringe is filled with the desired amount of the fluid, the syringe is used to pierce the self-sealing rubber septum (215) that seals the inlet port (212) of the disposable part (200), as shown in FIG. 9b. The syringe is inserted into the inlet port (212) so as to create fluid communication between the syringe and the reservoir (220). Once the syringe is inserted, a transfer of fluid from the syringe into the reservoir (220) begins, as illustrated in FIGS. 9c-e. As the fluid is being transferred, the air contained in the reservoir (220) is purged via the outlet port (213). As soon as the reservoir is full, the fluid begins to drip from the outlet port (213), as illustrated in FIG. 9f, which evidences that filling and priming procedures are completed. One of the purposes of the priming procedure is to eliminate any air contained within reservoir (220), so that during fluid delivery to the patient, no air is delivered. After completion of the filling and priming procedures/stages, the patient can connect the disposable part (200) and the reusable part (100) and begin using the dispensing unit (10).

Figure 10A:
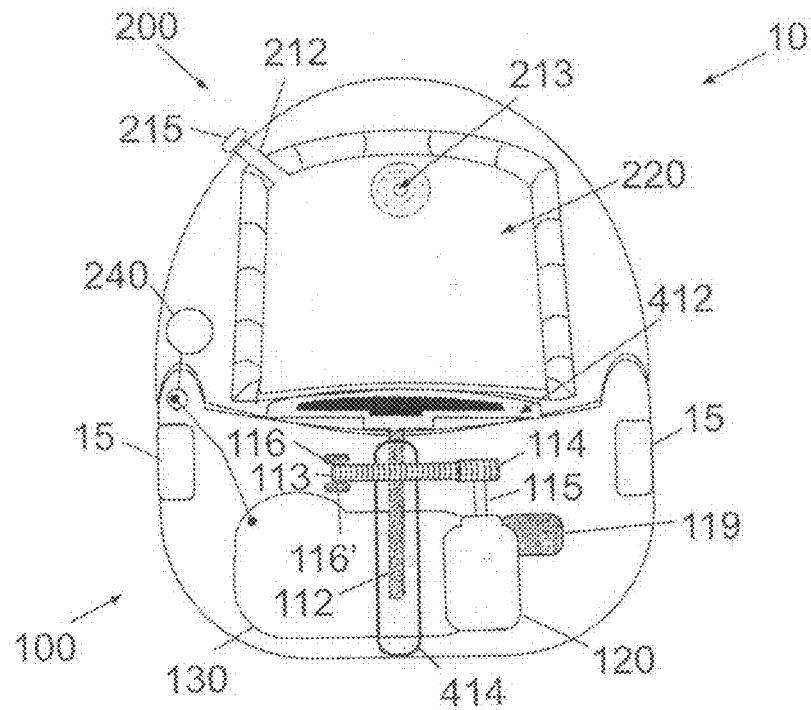
FIGS. 10a-c illustrates the flexible reservoir being pushed upon by a plunger, according to some embodiments of the present invention.
Figure 10B:
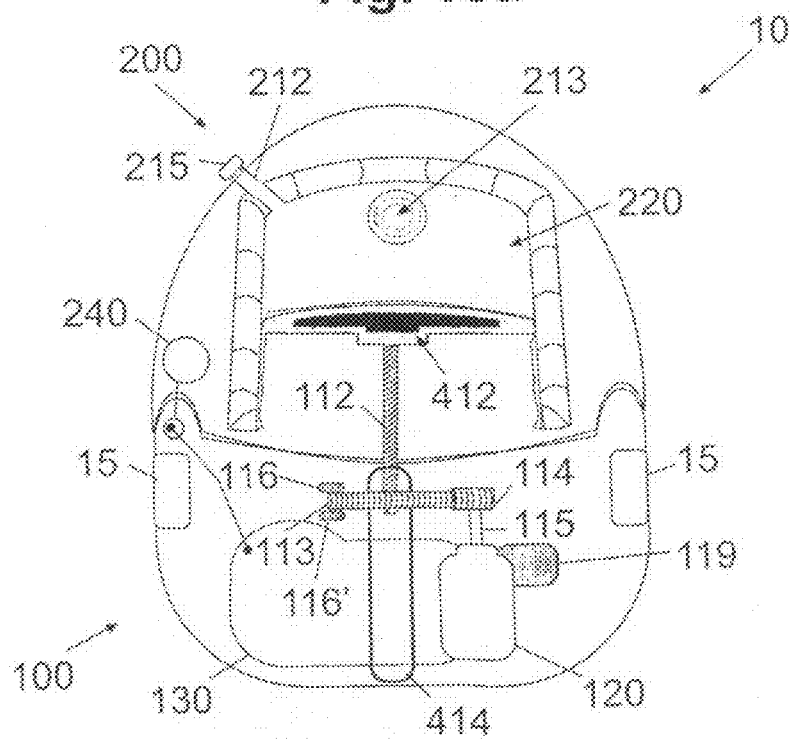
Figure 10C:
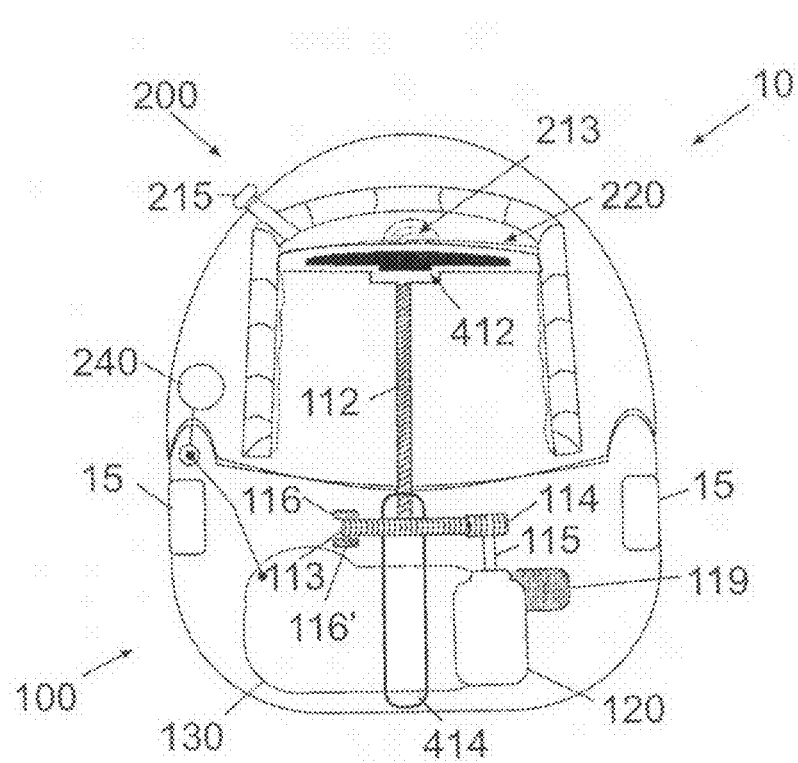

FIGS. 10a-c show exemplary driving and pumping mechanisms of the dispensing unit (10), according to some embodiments of the present invention. The driving and pumping mechanisms include a motor (120), a pinion (114), a secondary gear (113), a shaft (115), securing elements (116), (116'), a rotation monitoring mechanism (119), the lead-screw (112), the plunger (412), and a restraining component (414).

The motor (120) rotates the shaft (115), which is coupled to the pinion (114). Rotation of the shaft (115) rotates the pinion (114). The pinion is further coupled to the secondary gear (113). The pinion (114) includes teeth that are meshed with teeth of the secondary gear (113), so that the teeth of the pinion (114) transmit force and rotational motion (i.e., torque) to the teeth of the secondary gear (113), thus, causing the gear (113) to rotate. Rotation of the pinion (114) causes rotation of the gear (113) in an opposite direction. The secondary gear (113) has a central threaded bore that interacts with the threads on the lead-screw (112). Rotation of the secondary gear (113) causes translation of the lead-screw (112), which is in turn connected to the plunger (412). Thus, rotational motion of the threaded bore of the secondary gear (113) translates the plunger (412) toward the reservoir (220), thereby pushing upon the reservoir (220) and causing displacement of the fluid inside the reservoir toward the outlet port (213). Two securing elements (116, 116') (e.g., two protrusions) prevent the secondary gear (113) from shifting sideways. Additionally, another restraining component (414) can be provided, which prevents the lead-screw (112) from rotating, thus, urging the plunger (412) to be displaced uniformly and linearly toward the reservoir (220). As stated above, when the plunger (412) is linearly displaced by the lead-screw (112) it pushes upon the flexible reservoir (220), and thus, the fluid within the reservoir (220) is urged to flow toward the outlet port (213) and to the patient therefrom.

FIGS. 10b-c show the plunger (412) during linear displacement toward the reservoir (220) at various points. As the flexible reservoir (220) is being pushed upon by the plunger (412), a portion of the reservoir (220) is folded into its interior ("reverse sock effect"). After reservoir is empty, the plunger (412) can be withdrawn back into the reusable part (100) automatically before the disposable part (200) is separated from the reusable part, or manually upon said separation. Withdrawal of the plunger (412) can be done via a reverse rotational motion of the driving mechanism's components. Some of the advantages of the flexible reservoir (220) include the following: the reservoir (220) is capable of adjusting its size to fit precisely within the interior of the housing of the dispensing unit (10), thereby requiring less space; the reservoir allows a reduced rotational moment and/or torque applied by the motor, as there is no rubber seal and hence there is no associated friction against the rubber seal, as opposed to conventional tubular syringe plungers. The rotation monitoring mechanism (119) monitors rotational motion of the components of the driving mechanism. An exemplary rotation monitoring mechanism (119) includes a LED coupled with a light detector that detects light emitted by the LED, a photo-interruptor, or a "Hall effect sensor", or any other suitable monitoring device. An example of such device is disclosed in the co-owned/co-pending U.S. patent application Ser. No. 12/451,430, and International Patent Application No. PCT/IL2008/000642, both entitled "Methods And Apparatus For Monitoring Rotation Of An Infusion Pump Driving Mechanism" and claiming priority to U.S. Provisional Patent Application No. 60/928,751, filed May 11, 2007, the disclosures of these applications are incorporated herein by reference in their entireties.

The PCB (130) disposed in the reusable part (100) controls operation of the driving mechanism. The power supply (240) disposed in the disposable part (200) provides power to the PCB (130) and the driving mechanism. The PCB (130) can provide signals to the driving motor indicating the amount of liquid to be delivered (which corresponds to the length of translation of the plunger (412) inside the reservoir (220)).

Figure 11:
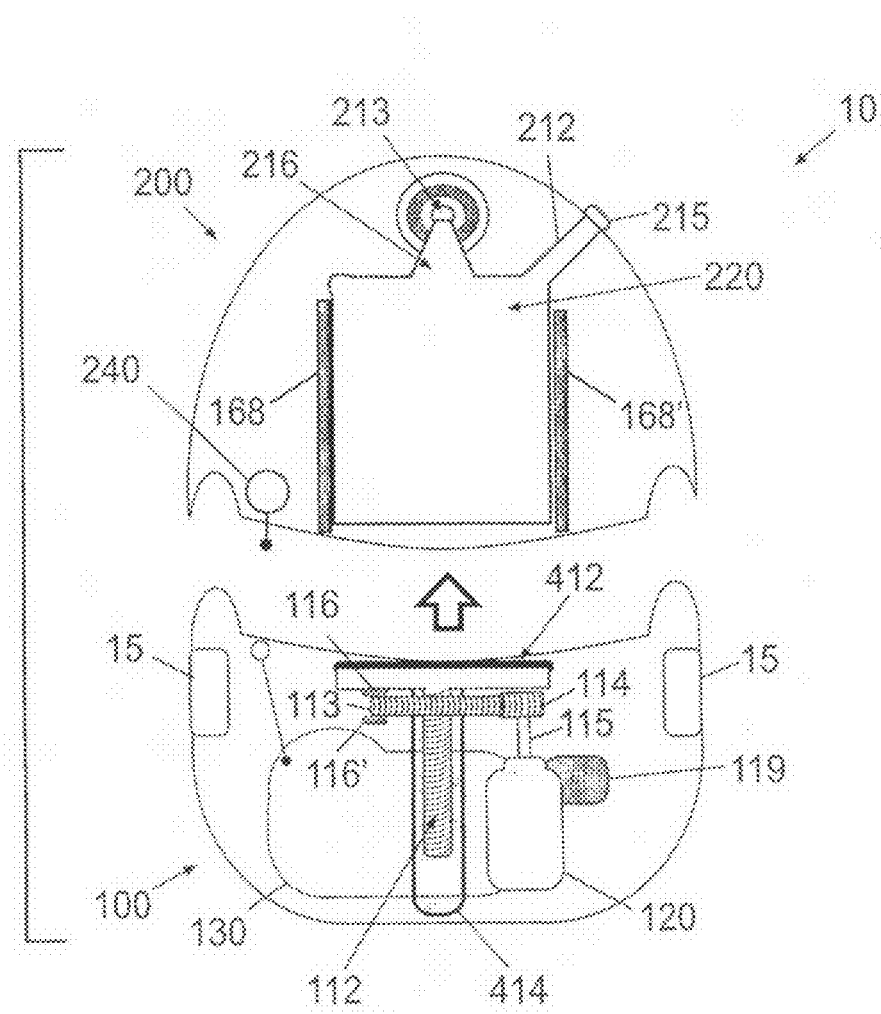
FIG. 11 illustrates exemplary components of the reusable and disposable parts of the dispensing unit, according to some embodiments of the present invention.

FIG. 11 shows another exemplary embodiment of the dispensing unit (10), according to the present invention. The dispensing unit (10) shown in FIG. 11 has the reusable part (100) and the disposable part (200) that have similar components shown in FIGS. 10a-c. Additionally, as shown in FIG. 11, the disposable unit (200) includes two parallel guides (168), (168') disposed within the housing of the disposable part (200) that confine the reservoir (220) to a preset space. The reservoir (220) is not attached to the guides (168), (168'). The guides (168), (168') constrain expansion and/or movement of the flexible reservoir (220). The reservoir (220) has a nozzle (216) which provides fluid communication with the outlet port (213). As the plunger (412) pushes the fluid in the reservoir (220), the fluid travels through the nozzle (216) and into the outlet port (213). In some embodiments, the reservoir (220) can be coupled to the outlet port (213) via a tube or any other suitable means.

Figure 12A:
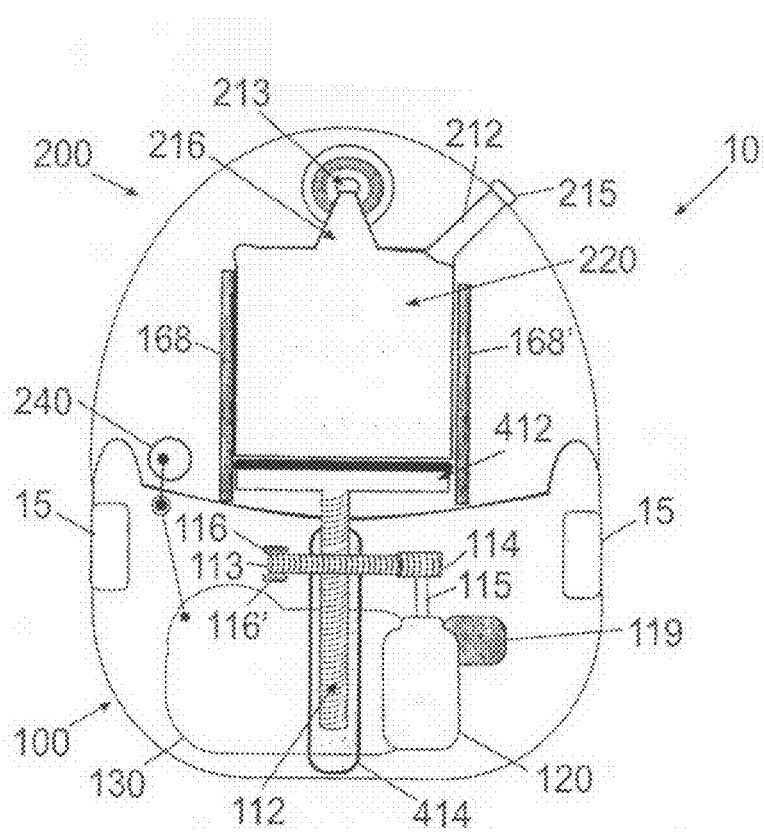
FIGS. 12a-b are top views of the flexible reservoir being pushed upon by the plunger, according to some embodiments of the present invention.

FIG. 12a shows the dispensing unit (10) having the pumping mechanism, wherein the plunger (412) is linearly displaced along an axis (parallel to the lead-screw (112)) by the lead-screw (112), which is driven by the driving mechanism's motor (120). When the plunger (412) is displaced in a forward direction, it pushes upon the flexible reservoir (220), thereby causing the fluid inside the reservoir to flow toward the outlet port (213).

Figure 12B:
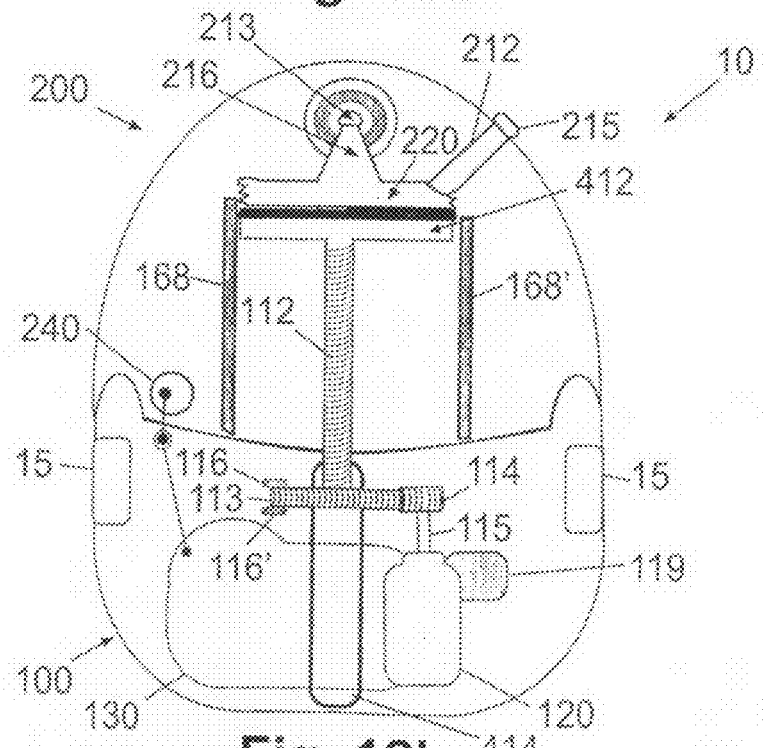

FIG. 12b shows the plunger (412) at a different stage and further pushing on fluid disposed inside the flexible reservoir (220). After reservoir emptying, the plunger (412) can be withdrawn back into the reusable part automatically before the disposable part (200) is separated from the reusable part, or manually upon disposable and reusable parts being separated.

Figure 13A:
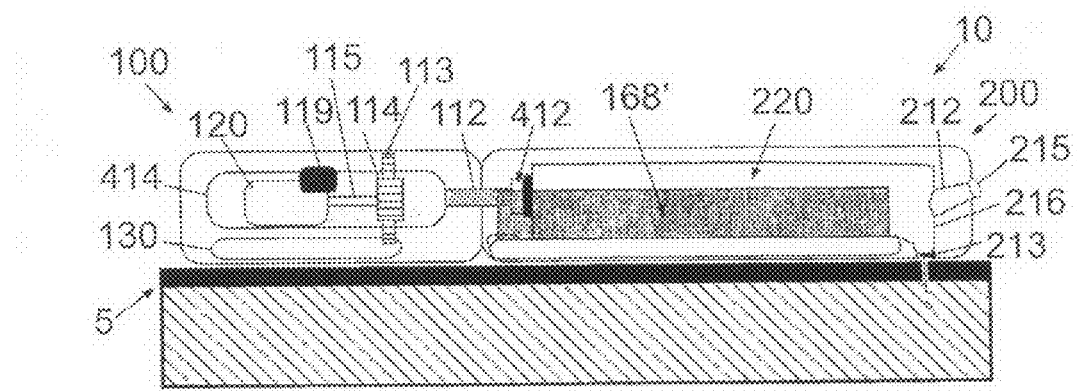
FIGS. 13a-b is a side view of the flexible reservoir being pushed upon by the plunger, according to some embodiments of the present invention.
Figure 13B:
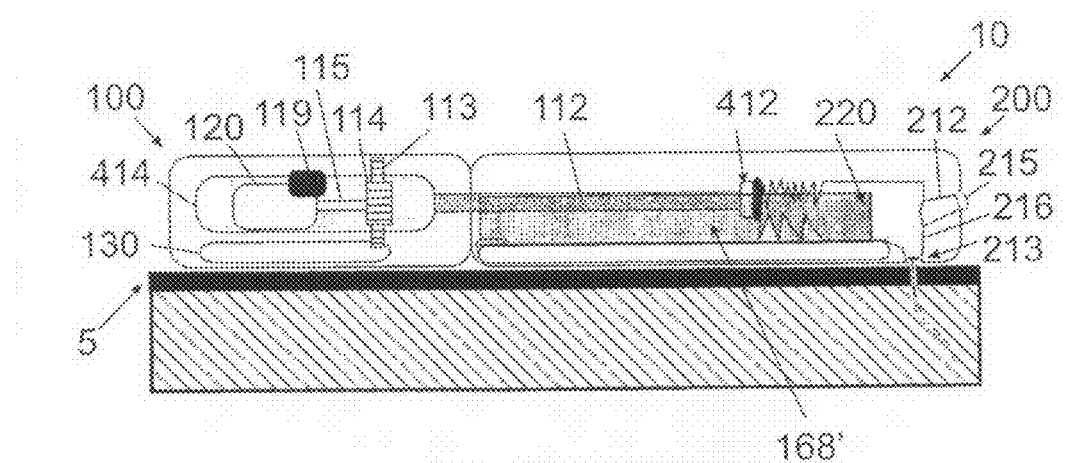

FIGS. 13a-b are side views of the dispensing unit (10) during the dispensing process. The side views correspond to the top views shown in FIGS. 12a-b, respectively. As shown in FIGS. 13a-b, the dispensing unit (10) is adhered directly to the skin (5) of the patient. Alternatively, the dispensing unit can be connected to a skin adherable needle unit (20) (as shown in FIG. 2a), where the needle unit (20) is adhered directed to the skin (5). Referring back to FIGS. 13a-b, as the plunger (412) begins to push upon the flexible reservoir (220), the reservoir (220) begins to compress between guides (168), (168'), which cause the reservoir (220) to begin folding near the outlet port (213), for example. As the reservoir (220) empties, the patient has an option to either refill the reservoir, as shown in FIGS. 9a-f, or replace the reservoir (220) (or the entire disposable part (200)). As stated above, the housing of the disposable part (200) and the guides (168), (168') prevent excessive expansion and encroachment of the flexible reservoir (220) beyond allotted space inside the disposable part (200). Further, because reservoir (220) is designed as a hermetic "sac" (with outlet and inlet ports being sealed by rubber septa), the fluid does not leak out from the reservoir and entry of contaminants is prevented.

Figure 14:
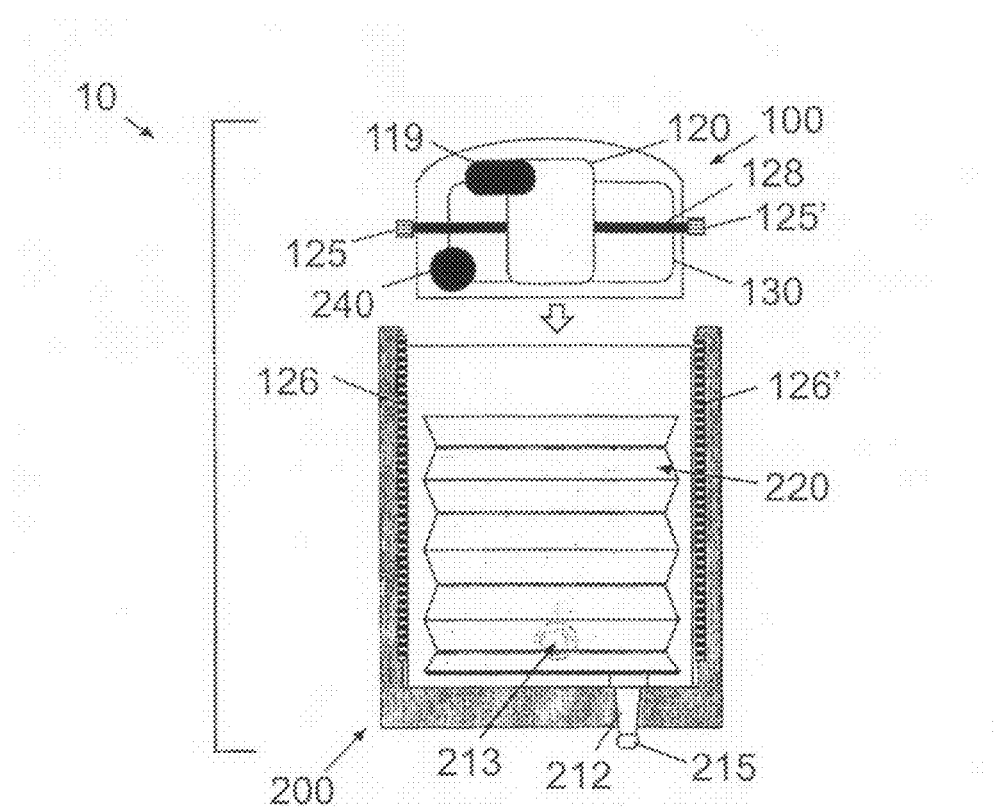
FIG. 14 illustrates exemplary components of the reusable and disposable parts of the dispensing unit, according to some embodiments of the present invention.

FIG. 14 shows another exemplary dispensing unit (10), according to some embodiments of the present invention. The dispensing unit (10) includes the reusable part (100) having the PCB (130) with electronics, the motor (120), a shaft (128), two cogwheels (125), (125'), an energy supply (240), and the rotation monitoring device (119). As stated above, the rotation monitoring device (119) can be a LED coupled with a light detector for detecting light emitted by the LED, a photointerruptor, or a "Hall effect sensor", etc. The disposable part (200) has two parallel racks/rails (126), (126'), and a concertina-like flexible reservoir (220) deployed between the rails (126), (126') along with other components discussed above. The concertina-like flexible reservoir (220) allows easy folding of the reservoir (220) during fluid dispensing procedures as well as easy unfolding during filling procedures. The reservoir (220) shown in FIG. 14 can have folding lines along which the reservoir (220) can fold and unfold. In some embodiments, a sac-like reservoir (similar to the one discussed above) may be used instead of the concertina-like reservoir shown in FIG. 14.

Upon connecting the reusable part (100) with the disposable part (200), fluid may be dispensed from the reservoir (220). When the two parts are connected, the motor (120), upon receiving signal(s) from the PCB (130) and being powered by the energy supply (240), begins rotating the shaft (128). Rotation of the shaft (128) causes rotation of the cogwheels (125), (125') coupled to the shaft (128). The cogwheels (125) and (125') include teeth configured to interact with teeth disposed along the rails (126) and (126'). As such, when the reusable part (100) is inserted into the disposable part (200), and the cogwheels (125) and (125') are aligned with respective rails (126) and (126'), rotation of the shaft (128) causes the reusable part (100) to translate along the length of the disposable part's housing. Such translation pushes upon the reservoir (220) causing fluid to be squeezed out from the outlet port (213) and folding the reservoir (220) in a concertina-like fashion. As the rails (126), (126') are parallel to each other, the translation along the rails is uniform and as such, the reusable unit (100) uniformly pushes upon the reservoir (220). The disposable part's housing prevents expansion of the reservoir (220) outside its allotted space. The reservoir (220) can be filled and primed as discussed above with regard to FIGS. 9a-f.

Figure 15A:
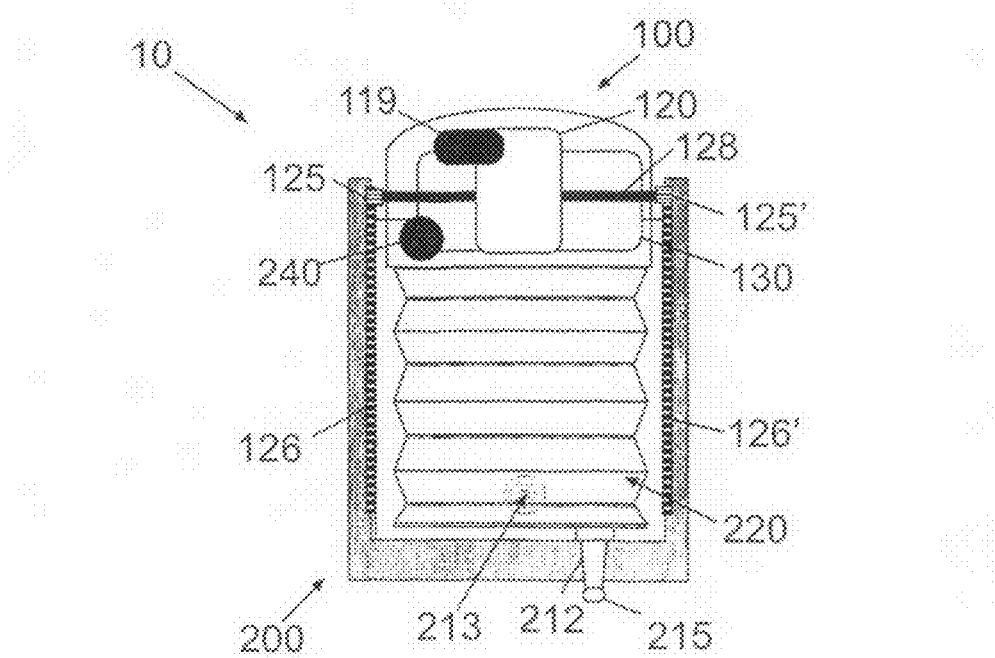
FIGS. 15a-c are top views of a concertina-like reservoir being compressed by the reusable part, according to some embodiments of the present invention.
Figure 15B:
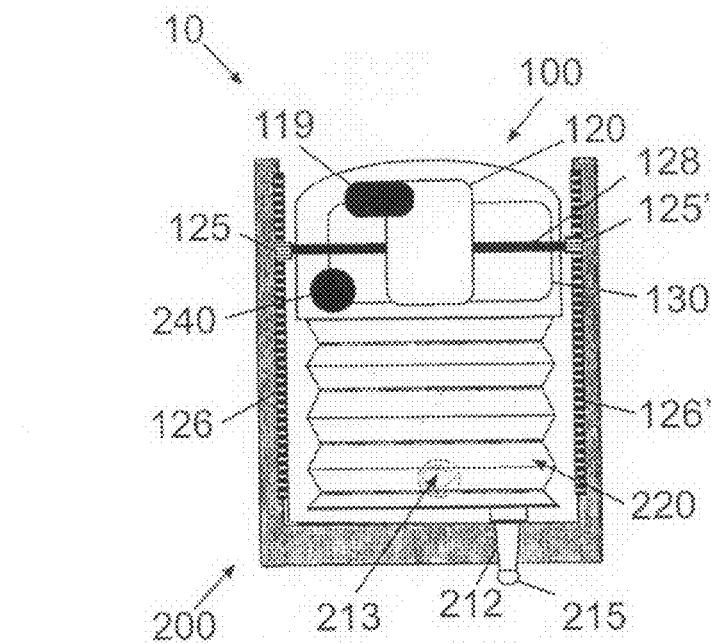
Figure 15C:
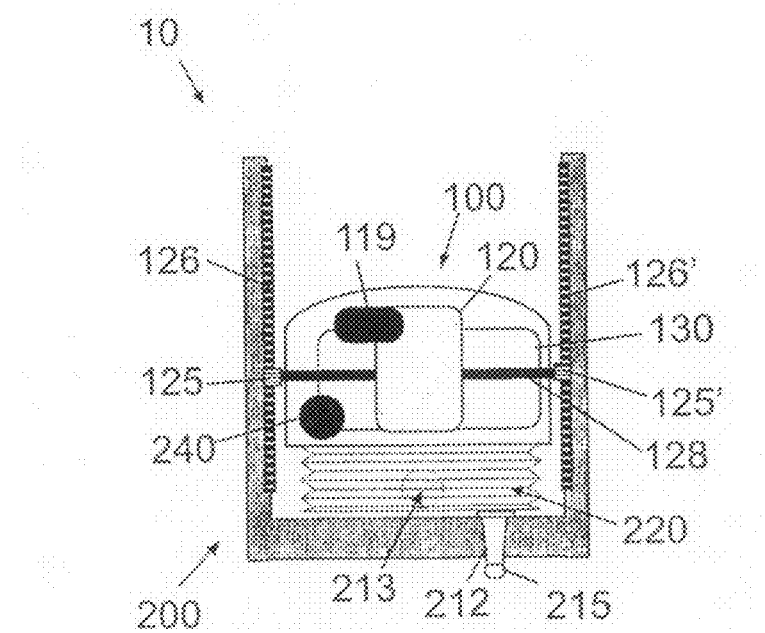
Figure 16A:
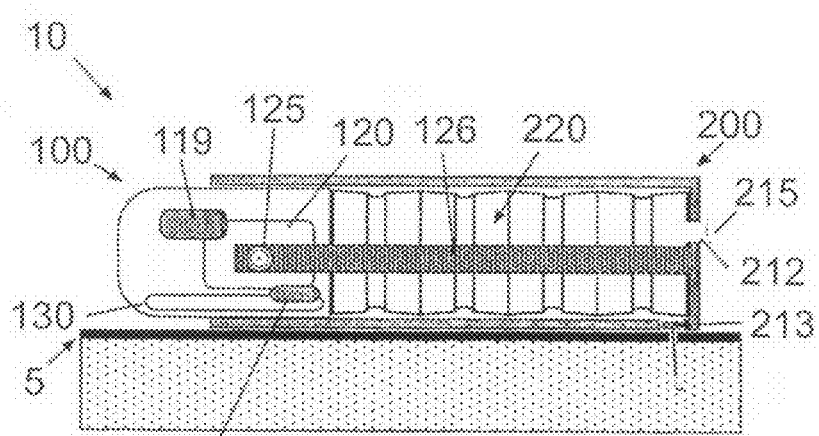
FIGS. 16a-c are side views of the concertina-like reservoir being compressed by the reusable part shown in FIGS. 15a-c.
Figure 16B:
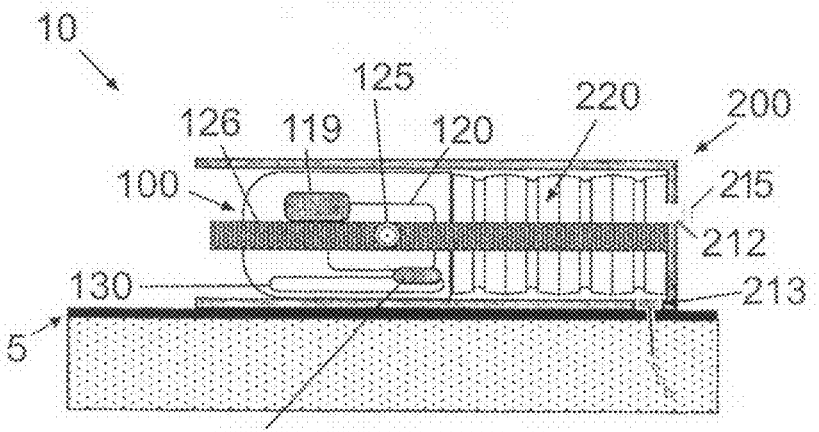
Figure 16C:
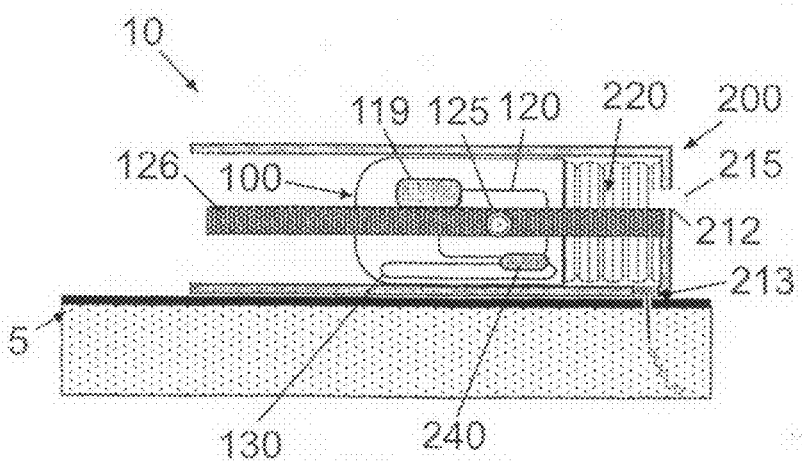

FIGS. 15a-c illustrate dispensing unit (10) shown in FIG. 14 during dispensing procedure. FIG. 15a shows an initiation of the pumping mechanism. The reusable part (100) is connected to (or inserted into) the disposable part (200). Upon connection, the cogwheels (125) (125') and respective rails (126), (126') come in contact with each other. The motor (120) begins rotating the shaft (128) and the cogwheels (125), (125') mounted on the shaft (128). As the cogwheels (125), (125') rotate on respective racks (126), (126'), the reusable part (100) is linearly displaced along the length of the disposable part (200), which results in compression of the concertina-like reservoir (220) and dispensing of fluid into the body of the patient via the outlet port (213). FIGS. 15b-c show the reusable part (100) further compressing the concertina-like reservoir (220). After all the fluid has been dispensed, the reusable part (100) can be mechanically shifted backwards. This can be accomplished manually or automatically using the reverse rotation of the motor (120). In some embodiments, the disposable part (200) can be discarded after each use of the device. Alternatively, the flexible reservoir (220) can be refilled using procedures shown in FIGS. 9a-f and the unit (10) can be used again. FIGS. 16a-c are side views of the dispensing unit (10) corresponding to FIGS. 15a-c. As shown in FIGS. 16a-c, the rails (126), (126') can be disposed in the middle housing of the disposable part (200). The cogwheels (125), (125') can be inserted into the rails (126), (126') during connection of the reusable part (100) and disposable part (200).

Figure 17:
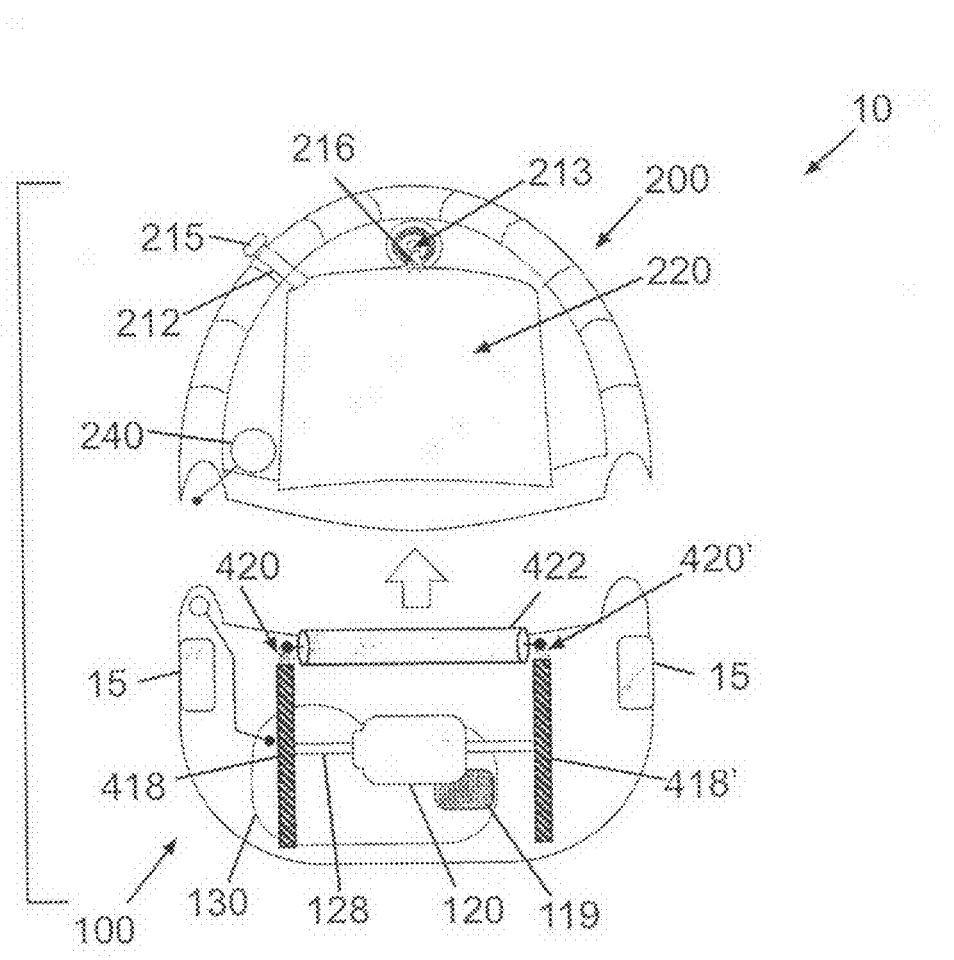
FIG. 17 illustrates exemplary components of the reusable and disposable parts of the dispensing unit, according to some embodiments of the present invention.

FIG. 17 shows another exemplary embodiment of dispensing unit (10), according to the present invention. The dispensing unit includes the reusable part (100) and the disposable part (200). The reusable part (100) includes the PCB (130) with electronics, the motor (120), the shaft (128), two gear racks (420), (420') (shown in more detail in FIG. 18b) each engaged with a respective gear wheel (not shown) coupled to the shaft (128), wherein rotation of the shaft (128) rotates the gear wheels causing movement of the racks (420), (420'). The gear racks (420), (420') are confined within respective sleeves (418), (418') having a rectangular cross-section. The sleeves (418), (418') are located in the reusable part such that they are opposite and parallel to each other. The reusable part (100) further includes an elongated roller (422), the opposite ends of which are affixed to the ends of the gear racks (420), (420'). The reusable part (100) also has manual buttons (15) and the rotation monitoring device (119), similar to the one discussed above. The disposable part (200) includes the flexible reservoir (220), the outlet port (213) and the energy supply (240). The reservoir (220) has the inlet port (212) sealed with the self-sealing rubber septum (215). The reservoir (220) has the nozzle (216) which couples the reservoir (220) with the outlet port (213). As can be understood by one skilled in the art, the reservoir (220) can also be coupled with the outlet port (213) via a tube or through any other suitable means. The bottom face of the reservoir (220) is secured, e.g., glued, welded, stabled, or otherwise secured, to the disposable part's (200) housing. As in the above embodiments, fluid dispensing is possible upon connection of the reusable part (100) with the disposable part (200). Filling and priming stages of the reservoir are similar to those explained above with reference to FIGS. 9a-f.

Figure 18A:
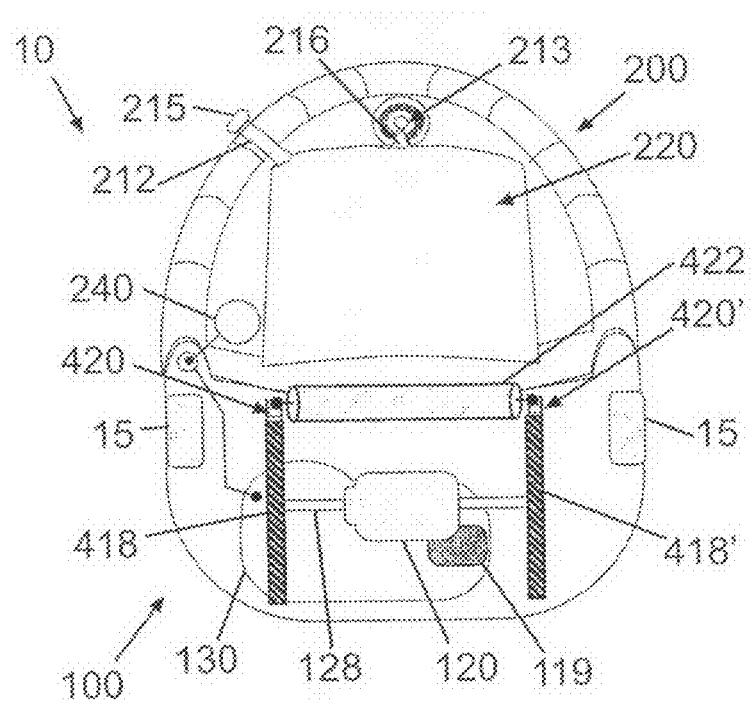
FIGS. 18a-c are top views of the flexible reservoir being flattened by a roller, according to some embodiments of the present invention.
Figure 18B:
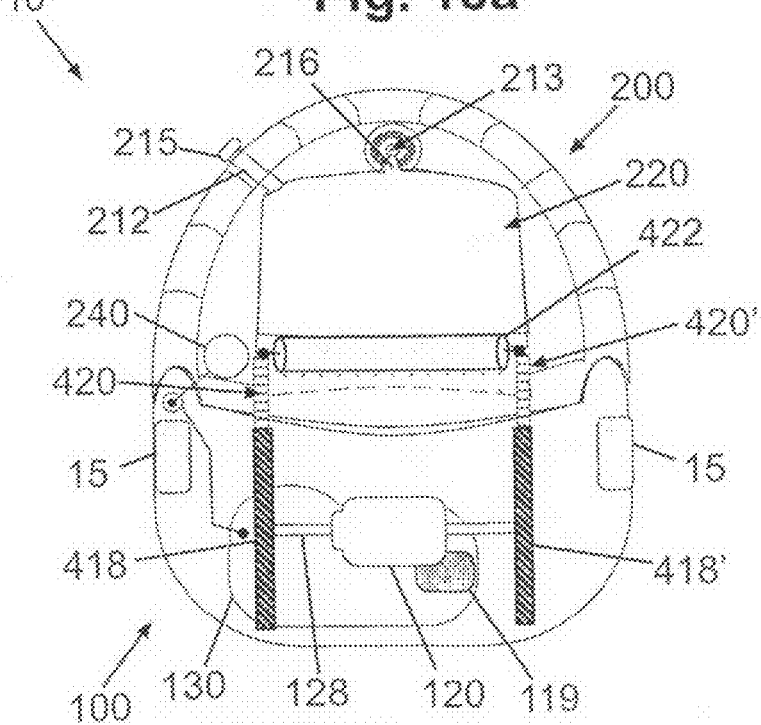
Figure 18C:
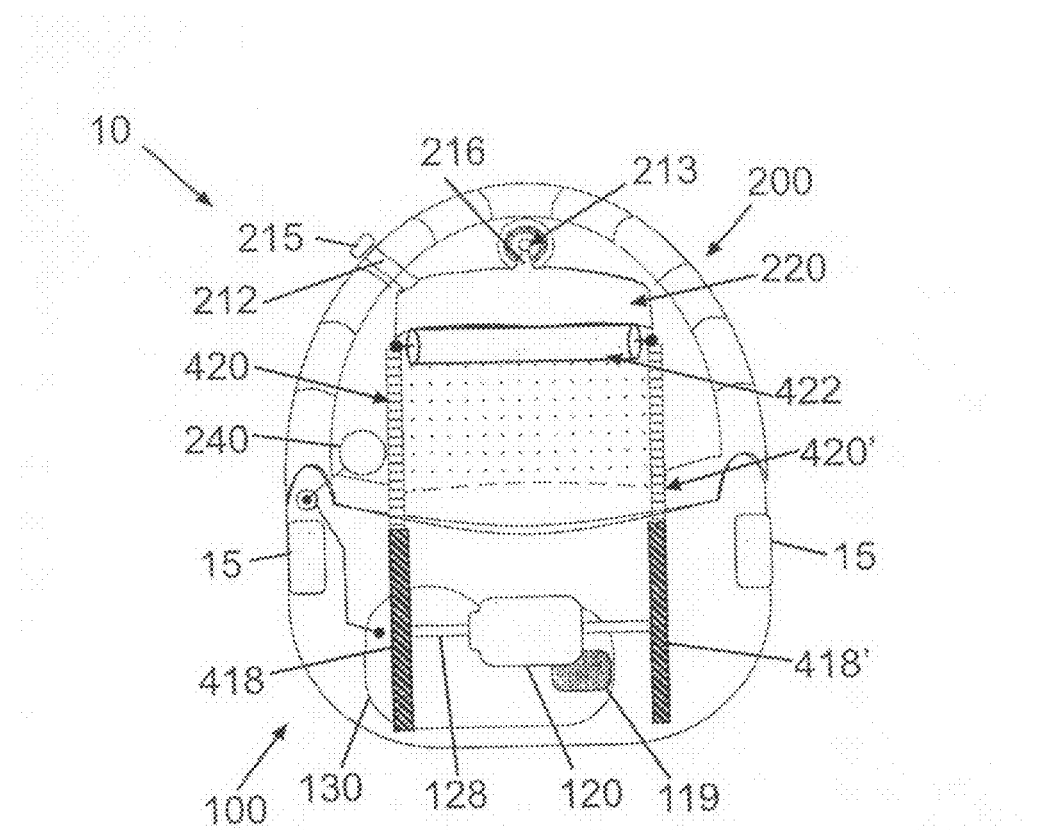
Figure 18D:
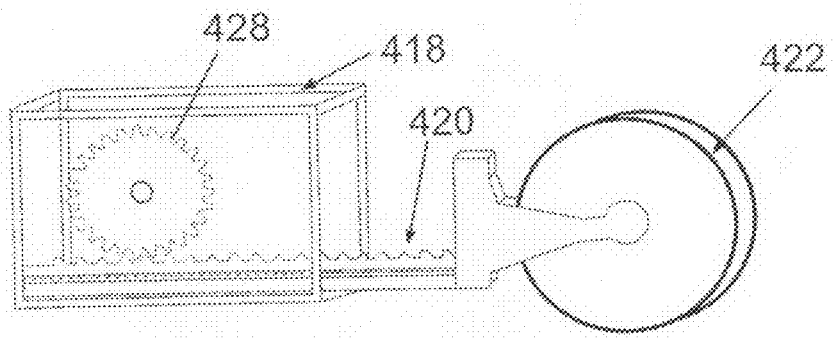
FIG. 18d is a partial side view of a rectangular tube and the driving mechanism components, according to some embodiments of the present invention.

FIGS. 18a-d show the dispensing unit (10) shown in FIG. 17, where the roller (422) is linearly displaced along the length of the reservoir (220) (or an axis parallel disposed along the length of the reservoir) using two parallel gear racks (420), (420'). As stated above, the racks (420) are coupled to respective gear wheels (as shown in FIG. 18d) driven by the motor (120). The gear racks (420), (420') are confined within respective sleeves (418), (418'). The opposite ends of the roller (422) are coupled to the racks (420), (420'). When the roller (422) is displaced forward it presses upon the flexible reservoir (220), thereby forcing the fluid within the reservoir (220) out via the outlet port (213).

It will be noted that an alternative pumping mechanism could be employed for linear displacement, e.g., as depicted in FIG. 10a, with the exception of the plunger being replaced by a roller. In this embodiment, the disposable part (200) can be similar to the one illustrated in FIG. 17.

FIGS. 18b-c show the roller (422) further flattening the flexible reservoir (220). After reservoir (220) emptying, the roller (422) can be withdrawn back into the reusable part (100) automatically before the disposable part (200) is separated from the reusable part, or manually upon said separation.

Figure 19A:
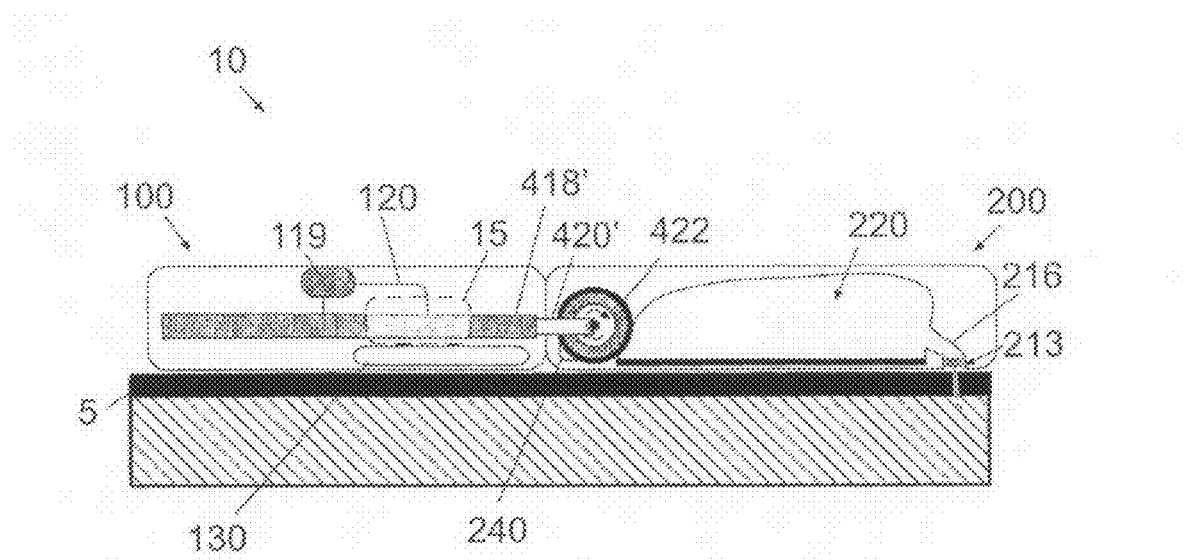
FIGS. 19a-c are side views of the flexible reservoir being flattened by a roller, according to some embodiments of the present invention.
Figure 19B:
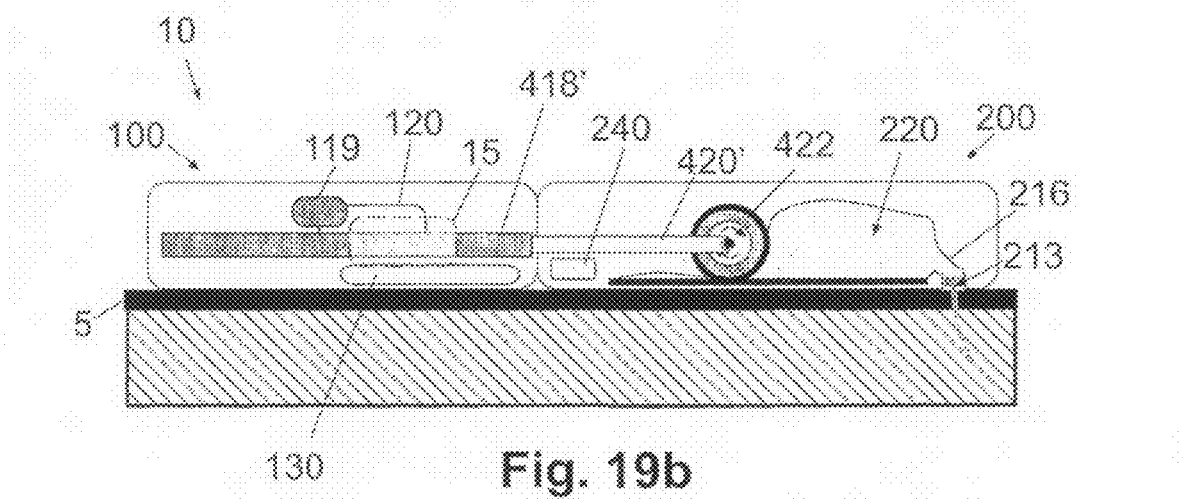
Figure 19C:
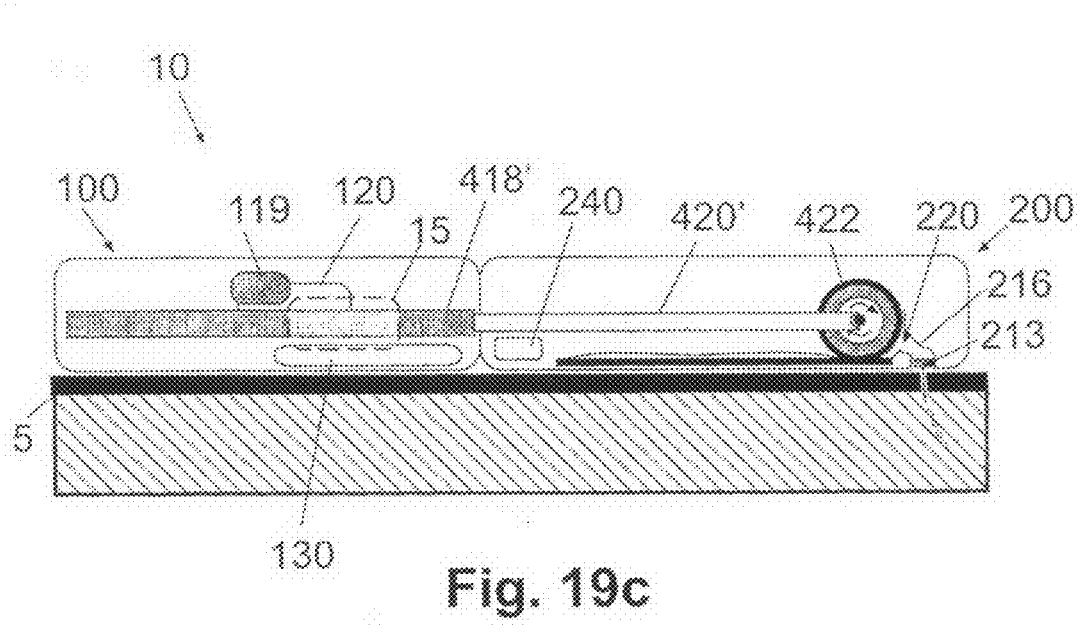

FIG. 18d shows a partial side view of one of the two sleeves (418), (418') (shown in FIGS. 19a-c) with confined therein gear rack (420) and gear wheel (428). The motor (not shown in FIG. 18d) rotates the gear wheel (428), and the rotational motion applied to the gear wheel (428) is converted into linear displacement of the gear rack (420) such that the gear rack displaces the roller (422), which is coupled to gear rack (420) at its end disposed outside the sleeve (418). In some embodiments, the sleeve (418) can be have a rectangular, square, oval, circular, or any other desired cross-section. FIGS. 19a-c are corresponding side views of the dispensing unit (10) shown in FIGS. 18a-c during dispensing of the fluid. As illustrated in FIGS. 19a-c, as the roller (422) translates along the length of the disposable part (200), it flattens the reservoir (220), thus, forcing the fluid from the reservoir (220) toward the outlet port (213).

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A skin adherable apparatus for delivery of a therapeutic fluid to the body of a patient, comprising:
    a dispensing unit comprising:
        a driving mechanism comprising at least a motor, a shaft coupled to said motor, and one or more cogwheel;
        a pump driven by said driving mechanism for delivering the therapeutic fluid to the body of the patient;
        a flexible reservoir separate from the pump and configured to be compressed by the pump to deliver the therapeutic fluid to the body of the patient from the flexible reservoir;
        one or more rails for guiding the pump therealong, the one or more rails being arranged adjacent to the flexible reservoir and extending at least a length along the flexible reservoir; and
        wherein the one or more cogwheel is configured to engage the one or more rails, and rotation of the shaft causes rotation of the one or more cogwheel, the one or more cogwheel configured to have teeth that engage teeth disposed along the one or more rails, causing a reusable part, placeable entirely above the reservoir and containing the motor, to translate along a length of a housing of a disposable part in a direction substantially perpendicular to a plane of shaft rotation, such translation pushing down upon the reservoir, causing the therapeutic fluid to be squeezed out from an outlet port and folding the flexible reservoir in a concertina-like fashion.

2. The apparatus according to claim 1, wherein the flexible reservoir is an enclosed flexible sac.

3. The apparatus according to claim 1, wherein the flexible reservoir has no internal sliding rigid elements.

4. The apparatus according to claim 1, further comprising a skin adherable needle unit, wherein said dispensing unit can be connected to and disconnected from said skin adherable needle unit.

5. The apparatus according to claim 1, wherein said dispensing unit becomes operative upon connection of said reusable part and said disposable part.

6. The apparatus according to claim 5, wherein said reusable part is provided with a reusable part housing accommodating therein at least a portion of said pump.

7. The apparatus according to claim 6, wherein said reusable part further comprises a rotation sensor.

8. The apparatus according to claim 6, wherein said disposable part is provided with the disposable part housing accommodating therein:
    the flexible reservoir;
    the outlet port coupled to the flexible reservoir for dispensing the therapeutic fluid to the body of the patient; and
    an inlet port coupled to the flexible reservoir for filling the flexible reservoir with the therapeutic fluid.

9. The apparatus according to claim 8, wherein said disposable part housing further accommodates a fluid delivery tube in fluid communication with the flexible reservoir and with said outlet port.

10. The apparatus according to claim 8, wherein said outlet port includes a self-sealing septum.

11. The apparatus according to claim 8, wherein said inlet port includes a self-sealing septum.

12. The apparatus according to claim 8, wherein said disposable part housing further accommodates a power supply for providing power to said dispensing unit; and
    wherein said reusable part housing further accommodates electronic components electrically coupled to said power supply and to said at least the portion of said driving mechanism for controlling operation of said at least the portion of said driving mechanism and said at least the portion of said pump.

13. The apparatus according to claim 8, wherein:
    the one or more rails are housed in said disposable part and arranged in parallel to a longitudinal axis of the flexible reservoir.

14. The apparatus according to claim 1, further comprising a remote control unit for one or more of: controlling operation of said dispensing unit, programming, data acquisition, and data downloading.

15. The apparatus according to claim 1, wherein said motor is selected from a group consisting of: a stepper motor, a DC motor, and a Shape Memory Alloy ("SMA") actuator.

16. The apparatus according to claim 1, wherein the flexible reservoir is configured for filling by a syringe.

17. The apparatus according to claim 1, wherein said therapeutic fluid is insulin.

* * * * *